United States Patent [19]

Bendiak

[11] Patent Number: 5,585,473

[45] Date of Patent: Dec. 17, 1996

[54] COMPOUNDS AND METHODS FOR MONOSACCHARIDE ANALYSIS

[75] Inventor: Brad K. Bendiak, Seattle, Wash.

[73] Assignee: The Biomembrane Institute, Seattle, Wash.

[21] Appl. No.: 352,278

[22] Filed: Dec. 9, 1994

[51] Int. Cl.⁶ .............................. C07H 5/04; C07H 5/06
[52] U.S. Cl. .................... 536/18.7; 536/17.2; 536/17.9; 536/18.2; 536/18.5; 536/123.1; 536/124
[58] Field of Search .................. 536/17.2, 17.9, 536/18.2, 18.5, 18.7, 123.1, 124

[56] References Cited

U.S. PATENT DOCUMENTS 4,719,294  1/1988  Rademacher et al. ............... 536/22
5,403,927  4/1995  Bendiak ............................ 536/124

FOREIGN PATENT DOCUMENTS 03227999  10/1991  Japan .

OTHER PUBLICATIONS

*The Carbohydrates*, Ed. by Pigman and Horton, vol. IB, pp. 929–939, (1980).

Bendiak et al. *Carbohydrate Research*, vol. 151, pp. 89–103, (1986).

Bendiak (*Glycobiology*, Abstract 1.14 & 1.15, vol. 2(5), (1992)).

Patel et al. *Biochemistry*, vol. 32, pp. 679–693, (1993).

*Primary Examiner*—John Kight
*Assistant Examiner*—Howard C. Lee
*Attorney, Agent, or Firm*—Seed and Berry LLP

[57] ABSTRACT

Compounds and methods are provided for use in monosaccharide analysis. The present invention discloses hydrazino monosaccharide derivatives. Methods for preparing and using hydrazino monosaccharide derivatives for structural analysis of aldose and ketose monosaccharides are also disclosed.

24 Claims, 20 Drawing Sheets

6-DEOXY-L-GALACTOSE
(L-FUCOSE)

3-O-METHYL-
D-GLUCOSE

2-AMINO-2-DEOXY-
D-GLUCOSE

D-GLUCURONIC ACID 2, 6-DIDEOXY-D-RIBO-
HEXOSE
(DIGITOXOSE)

2-C-HYDROXYMETHYL-
D-RIBOSE
(HAMAMELOSE)

ALDONONITRILE OF
D-GLUCOSE

DIETHYLDITHIOACETAL
OF D-GLUCOSE

COMPOUNDS AND METHODS FOR MONOSACCHARIDE ANALYSIS

TECHNICAL FIELD

The present invention relates generally to compounds and methods for monosaccharide analysis. This invention is more particularly related to hydrazino monosaccharide derivatives, their preparation and use for structural determination of aldose and ketose monosaccharides, and the incorporation of such compounds or methods into automated systems.

BACKGROUND OF THE INVENTION

Saccharides, which are also called sugars or carbohydrates, are major components of biological systems. Saccharides make up about 80% of the dry weight of plants, and are essential constituents of metabolic pathways in higher animals, either as monomers (monosaccharides) or as polymers which are composed of covalently linked monosaccharides (oligosaccharides). In addition, saccharides are often found as components of larger biological macromolecules, including proteins, lipids and nucleic acids. In this wide variety of forms, saccharides have a large number of critical functions in nature.

Because of the importance of saccharides in biological systems, procedures for unambiguous identification of monosaccharides, both free and as monomeric constituents of oligosaccharides, are of considerable utility. Furthermore, procedures for selectively identifying the monosaccharide at the end of an oligosaccharide are important for proof of polymeric saccharide structures.

Most monosaccharides in nature have a backbone structure that contains five carbon atoms (pentoses) or six carbon atoms (hexoses). In the linear form of these molecules, each backbone carbon atom may be covalently bonded to an oxygen atom, to form a series of hydroxyl groups (or modifications thereof) and a ketone or aldehyde group. Those molecules that contain an aldehyde group are referred to as aldoses, whereas those that contain a ketone group are known as ketoses.

In nature, most monosaccharides are aldoses. While members of each class of aldoses (e.g., pentoses and hexoses) are structurally similar, numerous distinct stereoisomers exist within each class. For example, in the hexose series, there are sixteen hexoses having an aldehyde group at C-1 and hydroxyl groups at all other positions along the carbon backbone. These sixteen stereoisomers are shown in FIG. 1 in their linear (Fischer projection) forms. (The Fischer projection represents the molecules so that the hydrogen atom and hydroxyl group on an asymmetric carbon atom come out of the plane of the paper towards the reader, as shown in the first molecule of FIG. 1.) Each stereoisomer is a different molecule, varying only in the stereochemistry at the different asymmetric carbon atoms.

Ketoses are also found naturally, usually having a ketone at the C-2 position (i.e., the second carbon of the carbon backbone) and hydroxyl groups at all other carbons, as shown below for D-fructose (the backbone carbons are designated as 1–6).

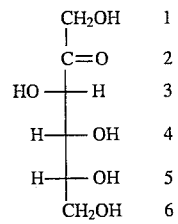

Ketoses may also have different numbers of carbons, there being, for example, hexoses and pentoses having a ketone function at C-2. In the hexose series of ketoses, there are eight stereoisomers having a ketone group at C-2. These hexoses are the D and L forms, respectively, of fructose, sorbose, tagatose, and psicose, each of which varies in the stereochemistry at the asymmetric carbons C-3 to C-5.

In addition to these variations in stereochemistry, hexoses and pentoses are also capable of existing in five-atom ring forms (also known as five-membered rings or furanoses) and six-atom ring forms (also known as six-membered rings or pyranoses). In these ring forms, an oxygen atom is present in the ring structure. For example, shown below are the five-membered and six-membered rings for D-glucose.

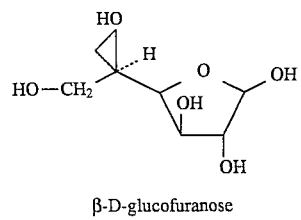
β-D-glucofuranose

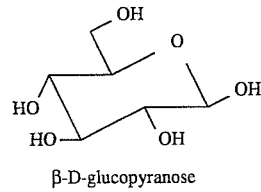
β-D-glucopyranose

In solution, aldose and ketose monosaccharides exist in equilibrium between the ring forms and the open chain forms, as shown in FIG. 1. Depending on the arrangement of the substituents at C-1, the ring form may be the α or the β anomer, as shown in the equilibrium for glucose below.

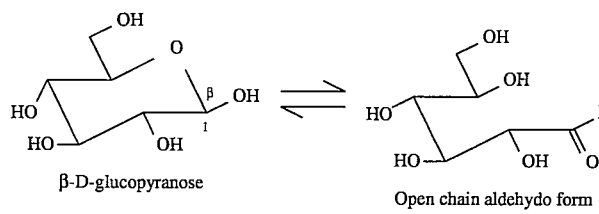 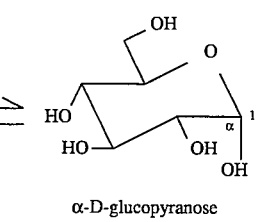

β-D-glucopyranose          Open chain aldehydo form          α-D-glucopyranose

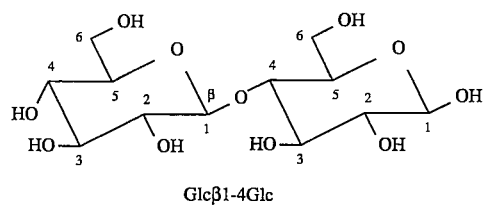

Glcβ1-4Glc

Monosaccharides that are capable of interconverting in solution to give the open chain forms may themselves be reduced (i.e., the carbonyl group converted to a lower oxidation state such as an alcohol), and are therefore referred to as reducing monosaccharides. Both free monosaccharides and monosaccharides located at one end (the reducing end) of an oligosaccharide may be reducing monosaccharides.

This large number of distinct monosaccharides that have the same elemental composition creates problems for identification of particular saccharides. For example, each of the 16 hexoses that have an aldehyde group at C-1 can exist in five forms (four cyclic forms and the linear form), which rapidly interconvert in solution. Consequently, during a chromatographic analysis, there are 16×5=80 possible forms of very closely related, interconverting molecules, rendering the chromatograms complex and often impossible to analyze.

Further complicating the monosaccharide analysis is the large number of such molecules that exist in nature which are modified in some way from the basic "core" structures discussed above. For example, there are common and abundant monosaccharides from many biological sources that lack one or more hydroxyl groups along the carbon backbone (termed deoxy-sugars if one hydroxyl group is lacking or dideoxy-sugars when two such groups are lacking), that contain an ether linkage instead of a hydroxyl group (usually a methyl ether, and termed methylated sugars), that have an amino group or N-acylamino group replacing a hydroxyl group (termed, respectively, amino sugars or acylamino sugars), or that have a carboxylic acid group instead of a $CH_2OH$ group at C-6 (termed uronic acids). Monosaccharides may also be branched, rather than having a linear carbon backbone (termed branched chain sugars). Hamamelose, shown in FIG. 2, is an example of a branched monosaccharide. In rare cases, monosaccharides may include combinations of these modifications, or may contain other modifications including, but not limited to, esters, cyclic acetals, sulfate esters and phosphate esters. Examples of some typical modifications are provided in FIG. 2.

Many monosaccharides are linked together to form oligosaccharides. In linear oligosaccharides, the monosaccharides are always linked together with the linkage from C-1 of one monosaccharide to one of C-2, C-3, C-4, C-5 or C-6 of another monosaccharide. For example, shown below is an oligosaccharide in which one D-glucose ("Glc") molecule is linked to another D-glucose molecule from C-1 of the D-glucose on the left side to C-4 of the D-glucose on the right side.

The bond between the two D-glucoses is termed a "glycosidic bond." The linkage between the two glucose molecules may be α or β, depending on the arrangement of the substituents at C-1 of the D-glucose on the left. The D-glucose on the right side of the di-glucose oligosaccharide structure possesses a hydroxyl group (at C-1) which may exist as an aldehyde group in the open chain form of that monomer. Therefore, the D-glucose on the right is the reducing monosaccharide. Conversely, the D-glucose on the left side of the structure does not possess a hydroxyl group at C-1 and, therefore, is termed a non-reducing monosaccharide.

Oligosaccharides contain no more than one reducing monosaccharide. In oligosaccharides that are linear (i.e., monosaccharides that are linked in a straight chain without branching), there will be one reducing end and one non-reducing end. If there is branching in an oligosaccharide (i.e., more than one monosaccharide is linked to a given monosaccharide), there will still be only one reducing end but two or more non-reducing ends. Since each monosaccharide may be linked to different positions of the adjacent monosaccharide, there is the potential for oligosaccharides of significant complexity. However, each reducing oligosaccharide possesses only one reducing monosaccharide (which may be an aldose or a ketose) which can exist in the open-chain form. As a result, there is the potential for unambiguous identification of the reducing aldose or ketose monosaccharide using reactions that modify only the carbonyl group on that monosaccharide.

Unambiguous identification of monosaccharides (either free or at the reducing end of oligosaccharides) has, however, proven to be difficult. Because of the enormous number of existing, distinct monosaccharides (many of which have similar or identical migration properties in chromatography) and the different interconverting forms of each monosaccharide, identification of a monosaccharide cannot be achieved with certainty based solely on its retention time in a chromatographic system. The use of mass spectrometry to identify monosaccharides is therefore essential, because the mass fragmentation spectral patterns (for example in electron impact mass spectrometry) clearly distinguish among the above classes of molecules. As long as all possible members of a class that give the same mass spectrum (such as, for example, all of the hexoses) are separable, the use of mass spectrometry permits monomers to be identified without doubt.

To limit the number of possible forms in which a monosaccharide may exist, and thus to improve the separation of members of each class by chromatography prior to mass spectrometry, derivatization techniques are often employed. Some derivatizations, however, can also result in cyclic products. Since there are usually four such products (α and β furanose and α and β pyranose derivatives), each monosaccharide can give rise to four chromatographic peaks in varying quantities. This makes analysis of complex mixtures difficult, if not impossible, due to the abundance of overlapping peaks.

Some modifications of monosaccharides that generate a single chromatographic peak have been described. The most useful of these convert the monosaccharide to a linear derivative that is incapable of cyclizing, and which therefore does not interconvert during chromatography. One procedure which has been employed extensively in the past involves the direct reduction of a monosaccharide aldehyde or ketone group to a hydroxyl group. This reaction converts an aldose or ketose to an alditol. Peracylation of alditols results in derivatives that are suitable for gas chromatography-mass spectrometry (GCMS). However, this procedure suffers from a serious limitation because some alditols may be generated from more than one monosaccharide. For example, as shown in FIG. 3, the same alditol product is generated by reduction of the molecules D-glucose and L-gulose. As a result, this procedure cannot distinguish between those two stereoisomers. Additional pairs of aldoses which give the same alditol product are L-glucose and D-gulose, D-altrose and D-talose, L-altrose and L-talose, D-galactose and L-galactose, and D-allose and L-allose. Among the aldoses, only D-mannose, L-mannose, D-idose and L-idose generate unique alditol products.

In addition, the reduction of a ketose generates a pair of alditols. For example, D-fructose generates D-glucitol and D-mannitol, D-sorbose generates D-gulitol and D-iditol, D-tagatose generates D-galactitol and D-talitol and D-psicose generates D-allitol and D-altritol. Thus, the formation of a given alditol upon reduction of a monosaccharide does not unambiguously identify the monosaccharide, since both ketoses and aldoses may generate the same alditols.

Other methods have been described for monosaccharide analysis that result in acyclic derivatives. For GCMS, the most useful derivatives for quantitation of monosaccharides are the aldononitriles (which may be generated from aldoses) and dithioacetals (which may be generated from aldoses and ketoses), since methods exist that achieve essentially quantitative yields of these derivatives. Representative examples of these derivatives are given in FIG. 4. These derivatization techniques have the important advantage that they yield a single product for each monosaccharide. For example, each of the 16 different aldose hexoses gives a unique derivative. Prior to analysis by GCMS, the aldononitrile derivatives are normally converted to acetyl esters and the dithioacetals are normally converted to trimethyl silyl ethers or trifluoroacetyl esters. The acetyl esters are stable, but the trimethyl silyl esters and trifluoroacetyl esters must be analyzed immediately after preparation and are very susceptible to cleavage by atmospheric water prior to and during analysis.

In addition, these derivatives cannot be used for analysis of a monosaccharide at the reducing end of an oligosaccharide. The synthesis of dithioacetals will, itself, cleave the glycosidic linkages, resulting in nonselective derivatization of the monosaccharide components of the oligosaccharide. Furthermore, dithioacetals are not stable under the acidic conditions required to cleave glycosidic linkages in oligosaccharides. While the formation of the aldononitrile may be achieved without cleavage of the glycosidic linkages, this derivative does not survive the acidic conditions needed to cleave the derivatized monosaccharide from the oligosaccharide.

Accordingly, there is a need in the art for a method of generating derivatives of free monosaccharides, as well as monosaccharides at the reducing end of an oligosaccharide, where the derivatives (1) permit unambiguous identification of each former monosaccharide, (2) are stable at room temperature and below for extended periods (i.e., more than one year), (3) survive conditions that cleave glycosidic linkages, thereby permitting identification of the monosaccharide at the reducing end of an oligosaccharide and (4) are amenable to on-line mass spectral analysis in techniques such as, but not limited to, GCMS, LCMS (liquid chromatography-mass spectrometry) and CZE (capillary zone electrophoresis-mass spectrometry), or are amenable to multiple fragmentation of daughter ions in procedures such as, but not limited to, GC-MSMS or GC-MSMSMS.

The present invention fulfills these needs and provides further related advantages.

SUMMARY OF THE INVENTION

Briefly stated, the present invention provides compounds and methods for monosaccharide analysis. In one aspect of the invention, hydrazino monosaccharide derivatives are provided, having the following structure:

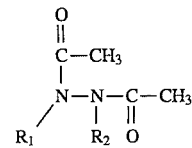

wherein $R_1$ is a 1-deoxy aldose moiety or a deoxy ketose moiety covalently bonded to N. Where $R_1$ is a 1-deoxy aldose moiety, the covalent bond to N occurs via the $C_1$ position. Where $R_1$ is a deoxy ketose moiety, the covalent bond to N occurs via the deoxy carbon in the sugar backbone, which was originally present in the ketone group. In all cases, $R_2$ is hydrogen or an alkyl group.

In a related aspect of the invention, methods are provided for preparing novel hydrazino monosaccharide derivatives. In one embodiment, the method comprises the steps of: (a) generating a hydrazone by reacting an aldose or a ketose with a hydrazine having the following structure:

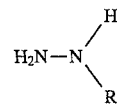

wherein R is hydrogen or an alkyl group; (b) reducing the hydrazone to a hydrazino derivative; and (c) acetylating the hydrazino derivative under conditions such that acetylation occurs on substantially all of the nitrogen atoms.

In another embodiment, the aldose or ketose used in step (a) is a monosaccharide located at the reducing end of an oligosaccharide, and the method additionally comprises the step of cleaving the derivatized aldose or ketose from the oligosaccharide.

In yet another embodiment, the method further comprises the step of fully acetylating the hydrazino monosaccharide derivative.

In a further related aspect of the present invention, methods are provided for structural analysis of aldose and ketose monosaccharides. In one embodiment, the method comprises the steps of: (a) generating a N,N'-diacetylhydrazino aldose or ketose monosaccharide derivative; (b) separating the monosaccharide derivative by chromatography; and (c) analyzing the separated monosaccharide derivative to determine the identity.

In a preferred embodiment, separation of the hydrazino monosaccharide derivative is by chromatography coupled to on-line mass spectrometry.

These and other aspects of the present invention will become evident upon reference to the following detailed description and attached drawings.

DETAILED DESCRIPTION OF THE INVENTION

Figure 1:
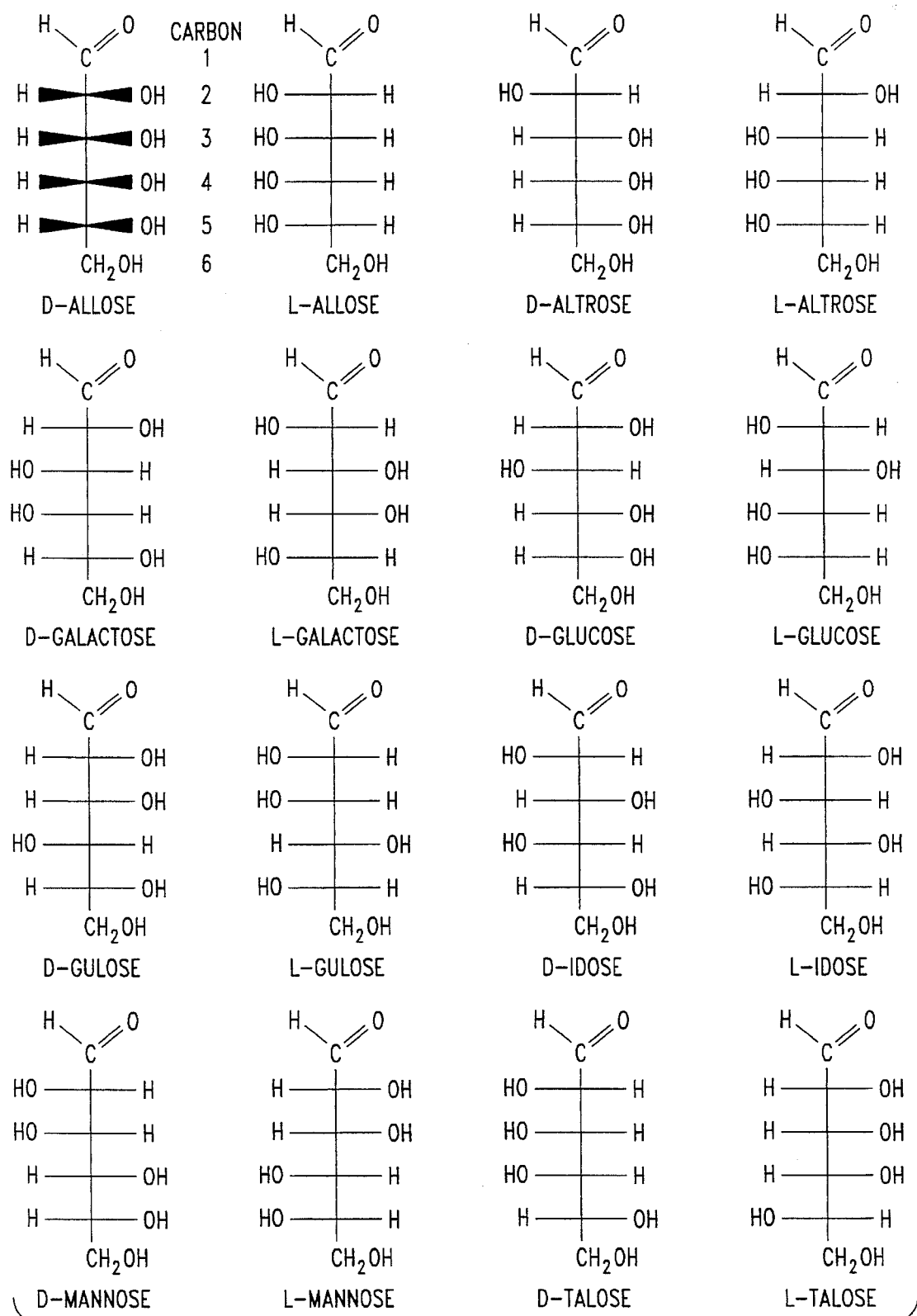
FIG. 1 illustrates the sixteen stereoisomers within the class of aldose hexoses having an aldehyde group at C-1 and hydroxyl groups at all other positions along the carbon backbone. The stereoisomers are shown in their linear forms, as Fischer projections. Each Fischer projection represents the molecule so that the hydrogen atom and hydroxyl group on an asymmetric carbon atom come out of the plane of the paper towards the reader.
Figure 2:
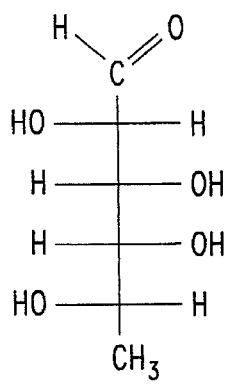
FIG. 2 illustrates some typical modifications of monosaccharides.
Figure 2:
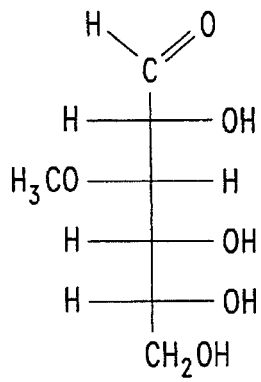
Figure 2:
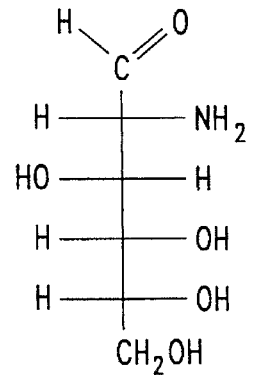
Figure 2:
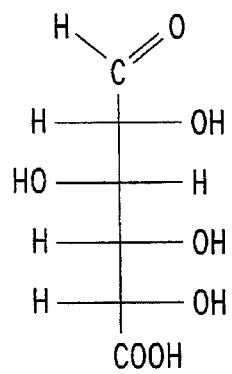
Figure 2:
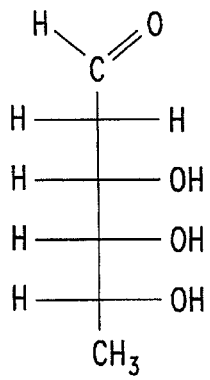
Figure 2:
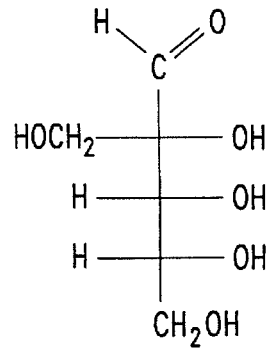
Figure 2:
Figure 3:
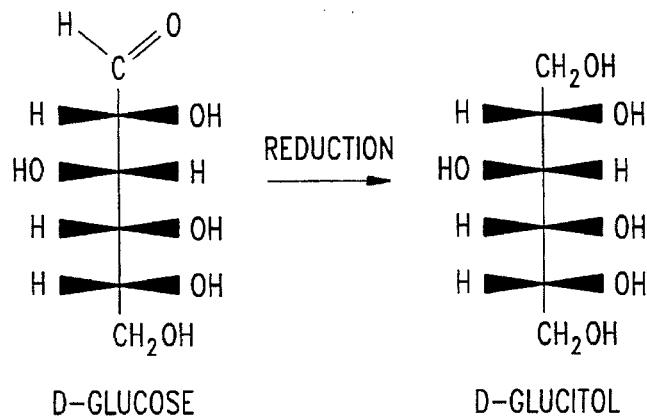
FIG. 3 illustrates the production of the alditol D-glucitol by reduction of D-glucose and L-gulose.
Figure 3:
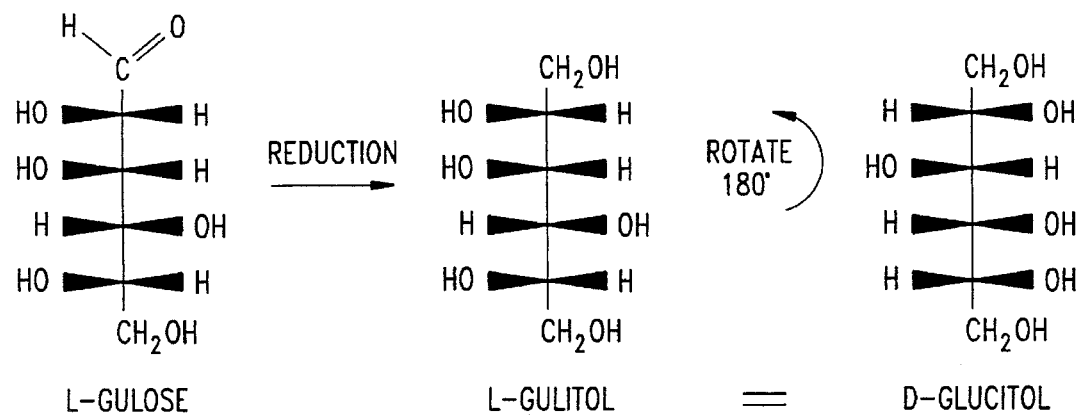
Figure 4:
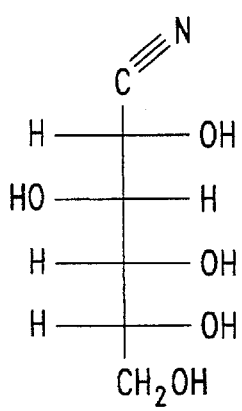
FIG. 4 illustrates the aldononitrile and diethyldithioacetal derivatives of D-glucose.
Figure 4:
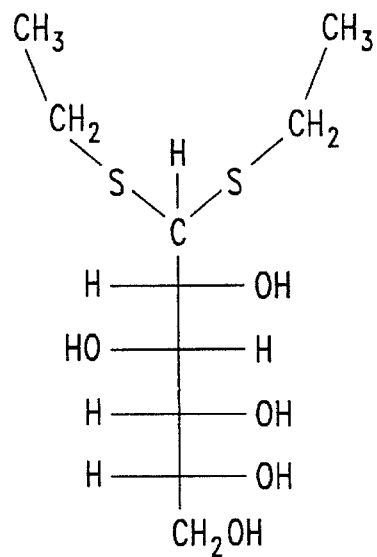
Figure 5A:
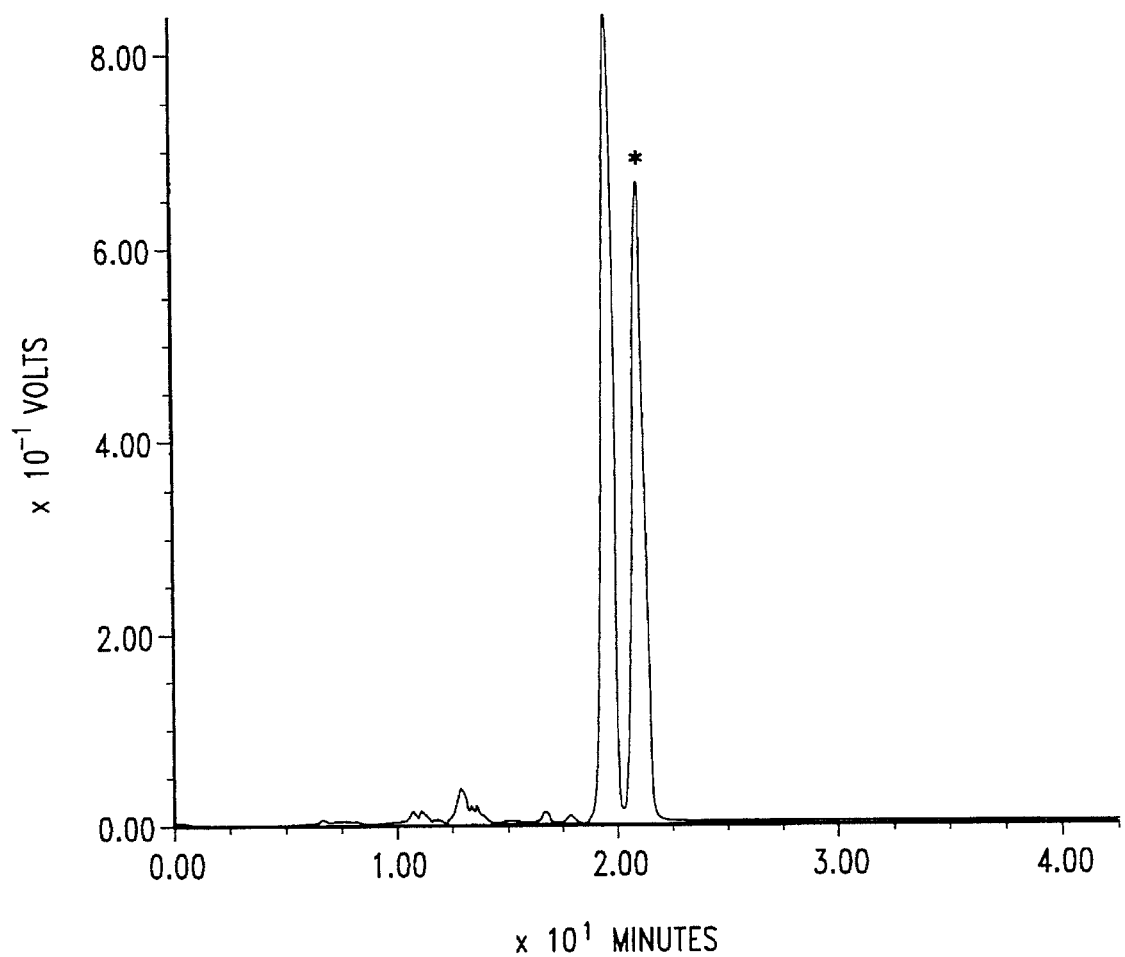
FIGS. 5a–g illustrate the elution profiles of some representative 1-deoxy-1-(N,N'-diacetylhydrazino) alditols.
Figure 5B:
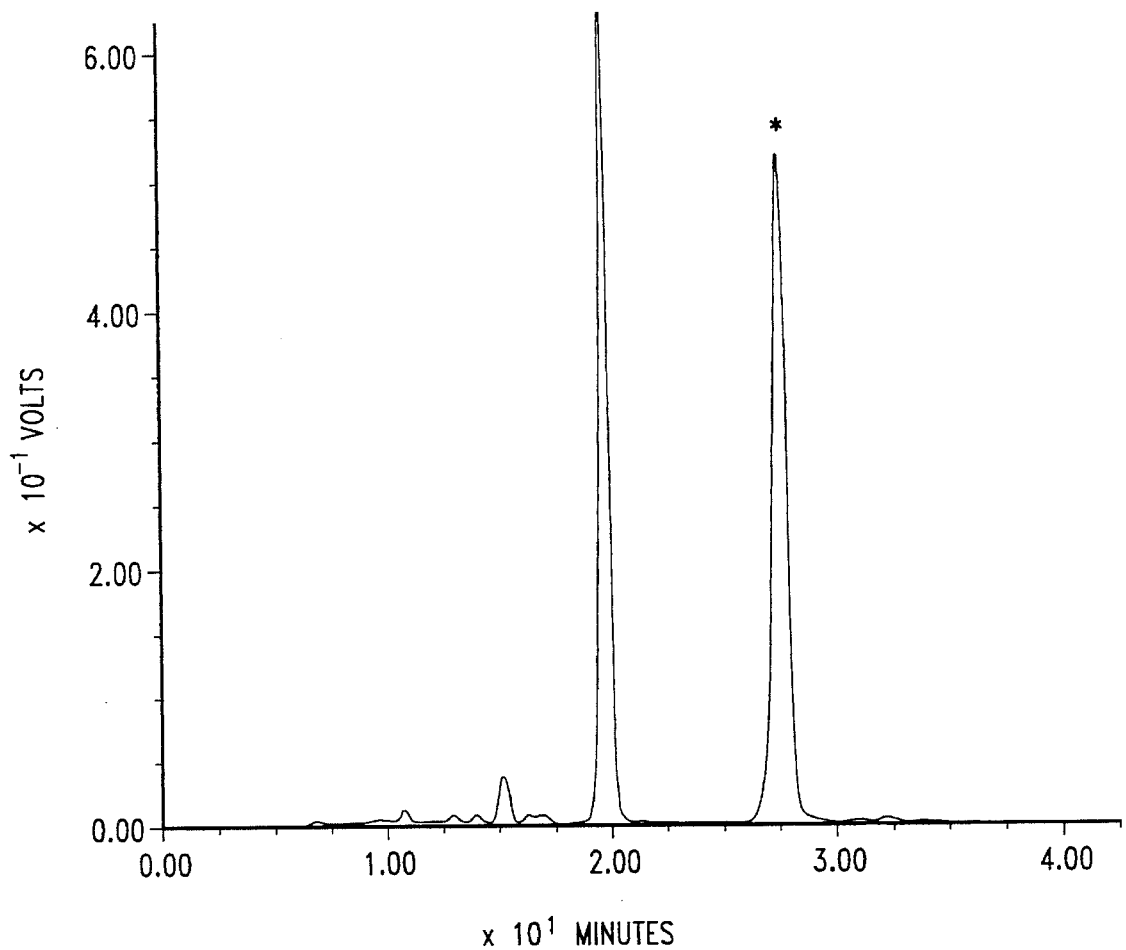
Figure 5C:
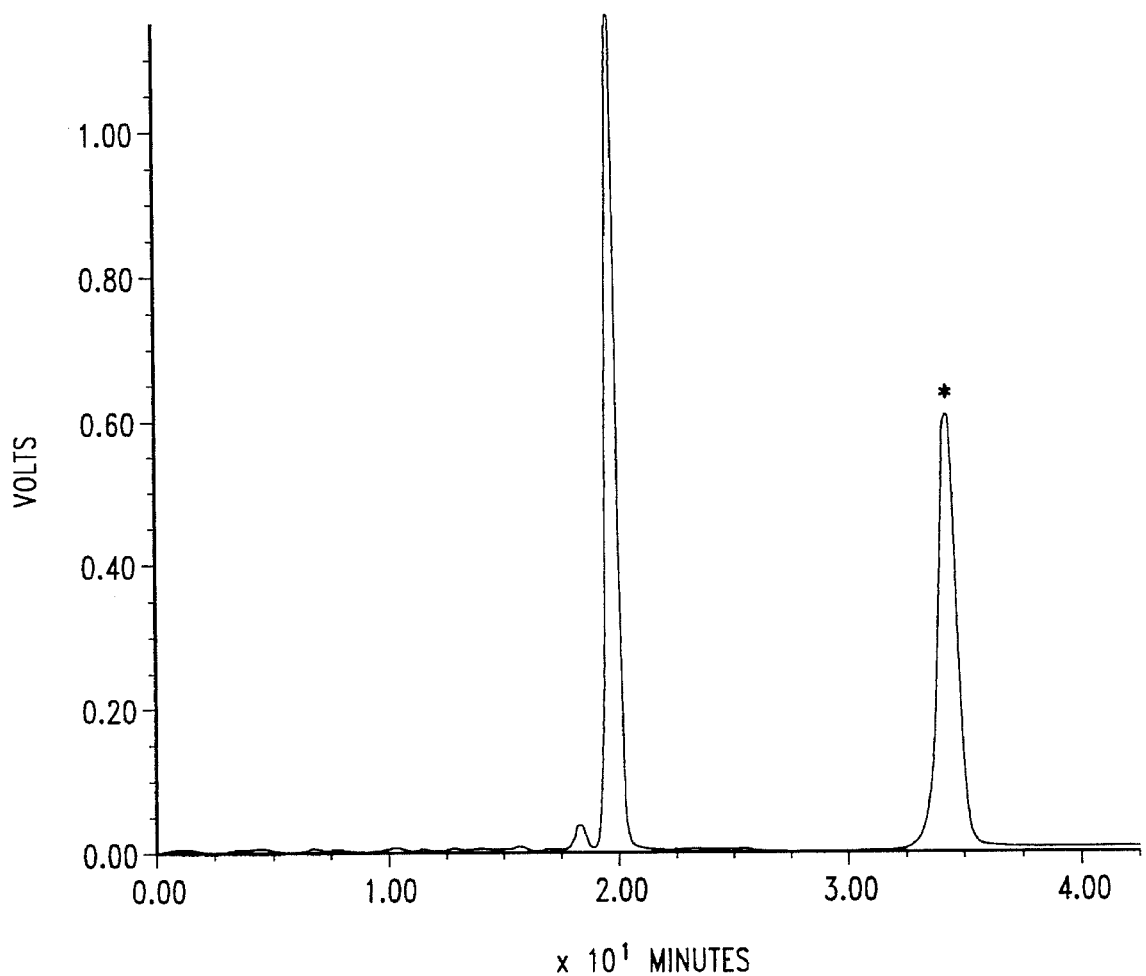
Figure 5D:
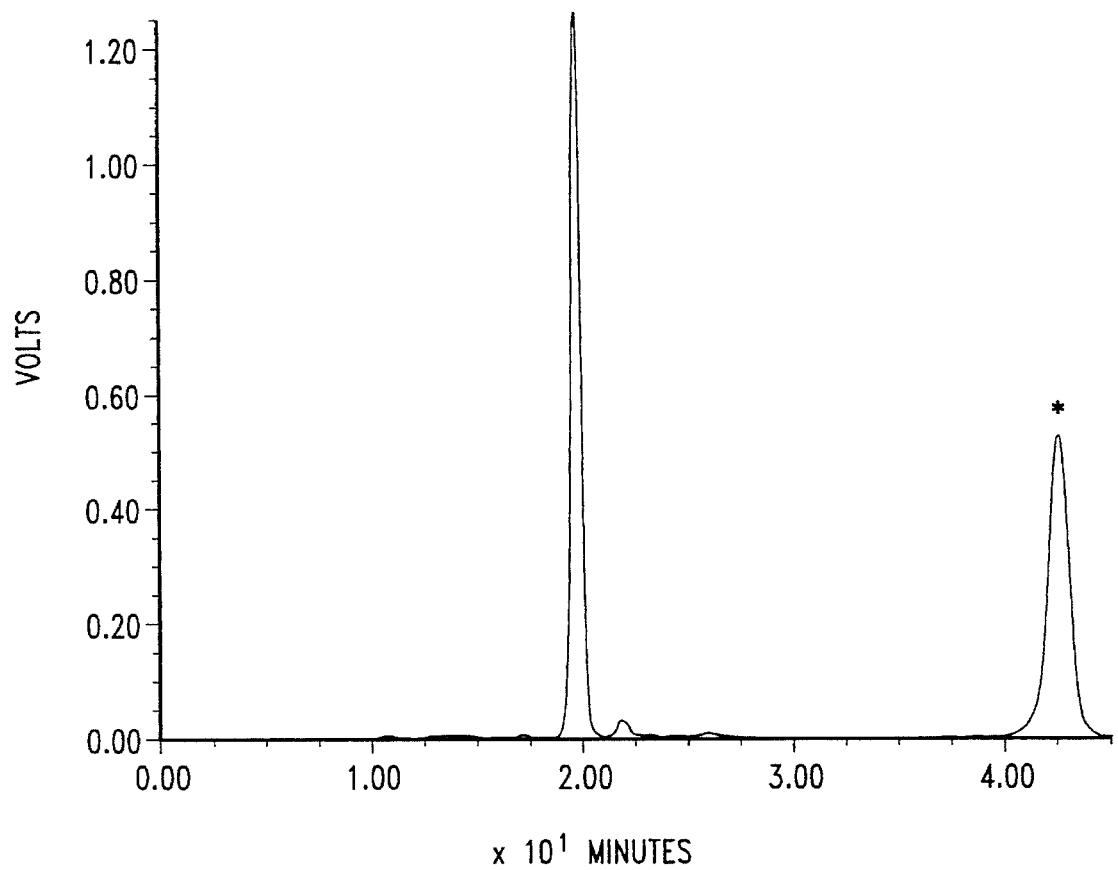
Figure 5E:
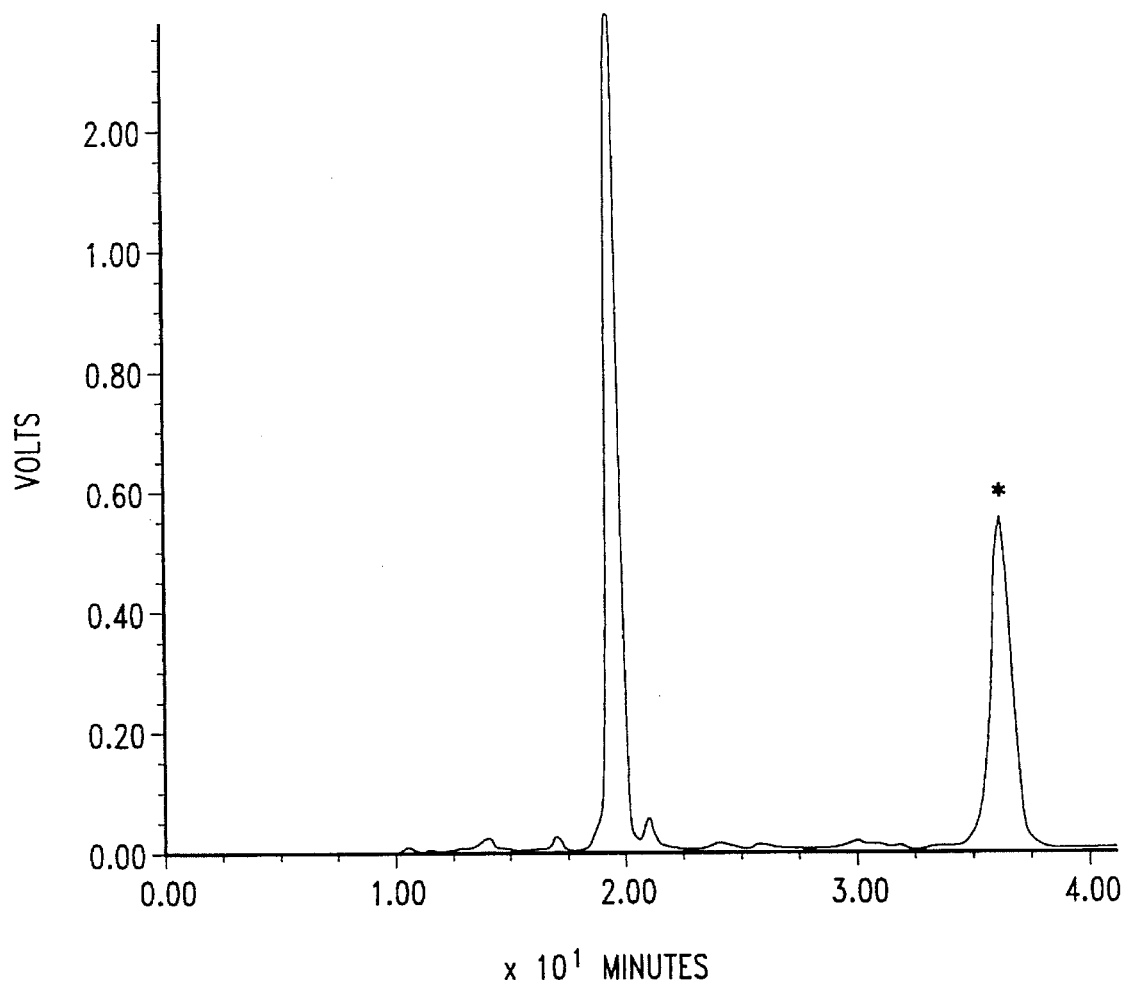
Figure 5F:
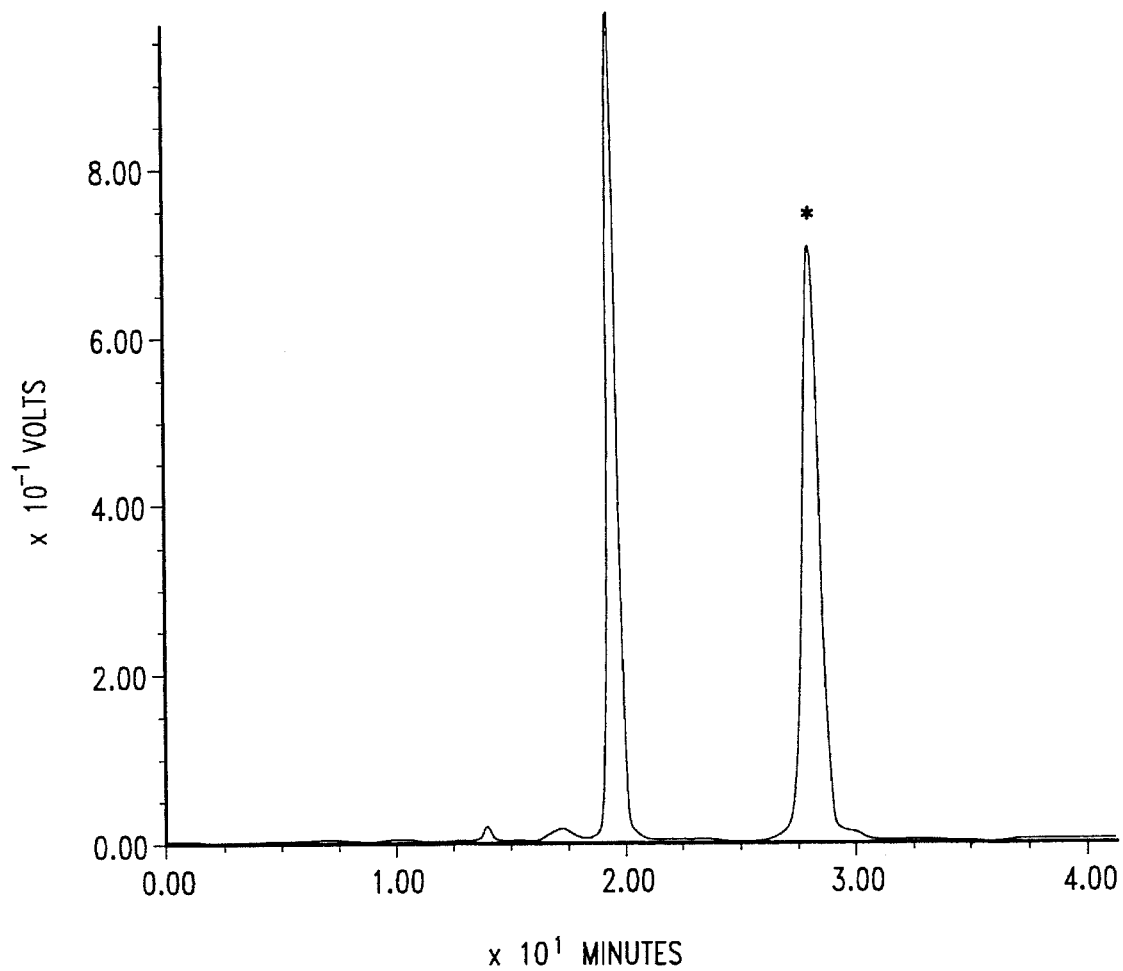
Figure 5G:
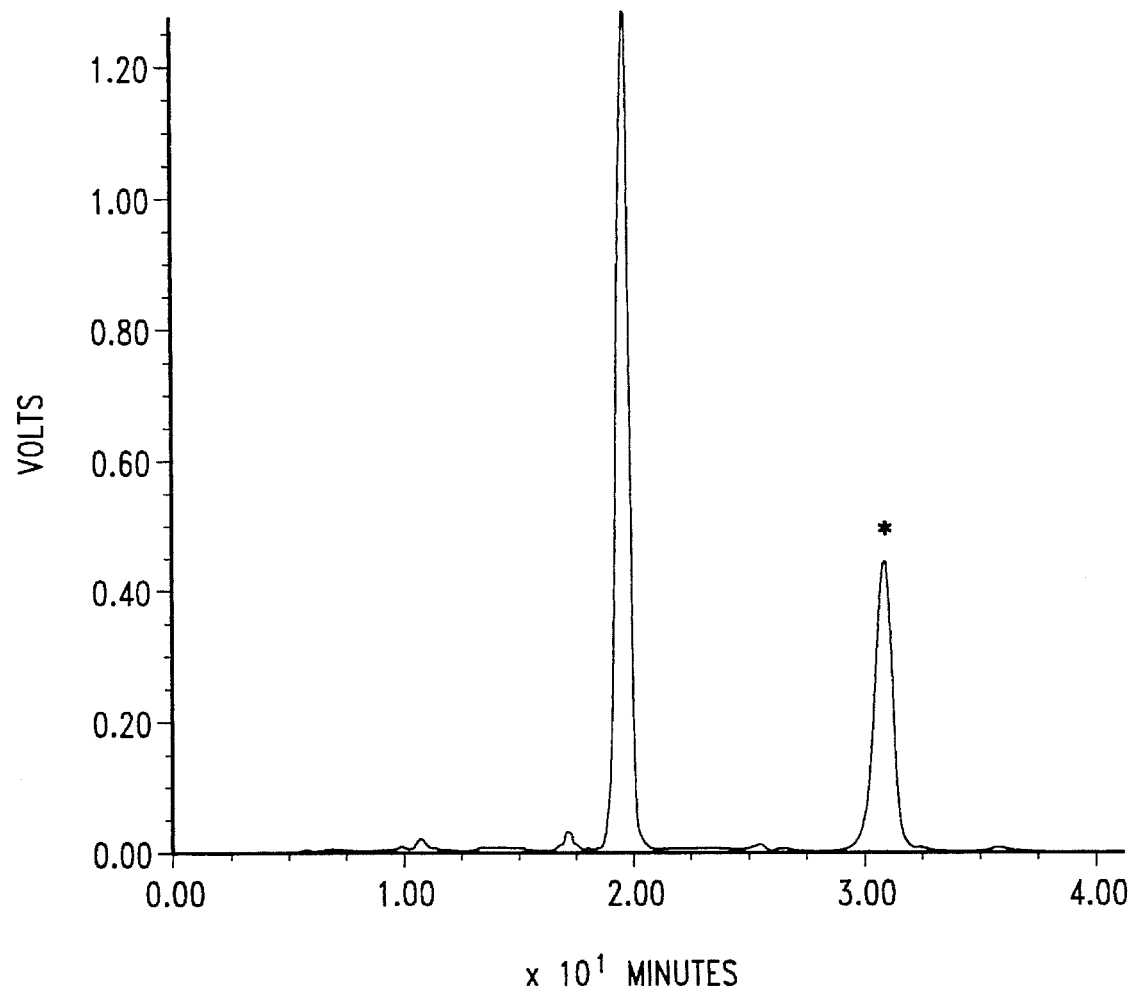

Prior to setting forth the invention, it may be helpful to an understanding thereof to set forth definitions of certain terms to be used hereinafter. In the context of this invention, a "saccharide" refers to any monosaccharide or oligosaccharide. A "monosaccharide" is a saccharide that is not hydrolyzable into smaller saccharide units. Monosaccharides include unsubstituted, non-hydrolyzable saccharides such as glucose, as well as modified saccharides in which one or more hydroxyl groups contain substitutions or have been replaced with hydrogen atoms (i.e., deoxy, dideoxy and trideoxy saccharides). A monosaccharide may be a "free monosaccharide," meaning that the monosaccharide is not covalently bonded to any other monosaccharides. Alternatively, a monosaccharide may be present within an oligosaccharide. "Oligosaccharides" are hydrolyzable saccharides that contain two or more monosaccharides linked together in a linear or branched manner. A "reducing monosaccharide" is a monosaccharide located at the reducing end of an oligosaccharide.

The term "aldose" is used to refer to a monosaccharide, either free or at the reducing end of an oligosaccharide, that may have an aldehyde group at the C-1 position. A "1-deoxy-aldose moiety" is a monosaccharide moiety in which the oxygen atom originally present within the aldehyde group at the C-1 position has been removed and replaced with a single hydrogen atom, such that the carbon atom at C-1 may be covalently linked to a second moiety.

For example, the 1-deoxy-D-glucose moiety has the following structure:

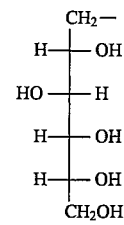

The term "ketose" is used to refer to a monosaccharide, either free or at the reducing end of an oligosaccharide, that may have a ketone group at any internal carbon atom along the backbone of the monosaccharide. A "deoxy-ketose moiety" is a monosaccharide in which the oxygen atom originally present within the ketone group has been removed and replaced with a single hydrogen atom such that the carbon atom originally present within the ketone group may be covalently bonded to a second moiety. For example, the 2-deoxy-D-glucitol moiety has the following structure:

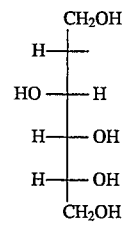

A 3- or 4-deoxy ketose moiety refers to a monosaccharide in which the ketone oxygen atom at the C-3 or C-4 position, respectively, has been removed and replaced by a single hydrogen atom.

An "acetylated" molecule is one in which one or more acetyl groups are covalently bonded to the molecule. A "fully acetylated molecule" is a molecule in which all of the free hydroxyl groups and nitrogen atoms have been derivatized to form acetyl esters, amides or hydrazides.

As noted above, the present invention is generally directed to compounds and methods useful for a variety of purposes, such as monosaccharide analysis. More specifically, this invention is directed to hydrazino derivatives of monosaccharides, as well as methods for preparing and using hydrazino monosaccharide derivatives, e.g., for analysis of free monosaccharides and monosaccharides at the reducing end of oligosaccharides.

The monosaccharide derivatives of the present invention may be generally represented by the following formula:

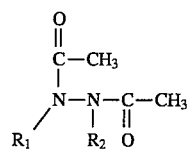

$R_1$ is a 1-deoxy aldose moiety or a deoxy ketose moiety that may be derived from any aldose or ketose monosaccharide, including free monosaccharides and monosaccharides at the reducing end of an oligosaccharide. Suitable monosaccharides include, but are not limited to, aldose hexoses such as D-glucose, L-glucose, D-allose, D-altrose, D-galactose, D-gulose, D-idose, D-mannose, and D-talose; ketose hexoses such as D-fructose, D-psicose, D-sorbose, and D-tagatose; aldose pentoses such as D-arabinose, D-lyxose, D-ribose, and D-xylose; aldose tetroses such as D-erythrose and D-threose; aldose trioses such as D-glyceraldehyde; and glycolaldehyde.

The aldose or ketose moiety may also be derived from a modified monosaccharide. Suitable modified monosaccharides include, but are not limited to, deoxy sugars such as 6-deoxy-L-galactose (L-fucose) and 6-deoxy-L-mannose (L-rhamnose), dideoxy sugars, trideoxy sugars, amino sugars such as 2-amino-2-deoxy-D-glucose and 2-amino-2-deoxy-D-galactose, acylamino sugars such as 2-acetamido-2-deoxy-D-glucose and 2-acetamido-2-deoxy-D-galactose, sugars having one or more O-alkyl ethers such as 3-O-methyl-D-glucose, uronic acids, branched-chain sugars, sugars having one or more sulfate or phosphate esters of the hydroxyl groups, or sugars having any combination of the above modifications. Representative combinations of these modifications include the combinations found in thevetose (6-deoxy-3-O-methyl-D-glucose) and vinelose (6-deoxy-3-C-methyl-2-O-methyl-L-talose), which is a branched-chain, dideoxy sugar having a O-methyl ether. Additional suitable monosaccharides may be found, for example, in the CRC Handbook of Chemistry and Physics, 68th edition (CRC Press, Inc. 1987) at C-705–C-710, which is incorporated herein by reference.

Preferably, $R_1$ is a 1-deoxy aldose moiety having a backbone of from 2 to 9 carbon atoms or a deoxy ketose moiety having a backbone of from 3 to 9 carbon atoms. More preferably, $R_1$ is a deoxy pentose or deoxy hexose moiety. Representative examples of the monosaccharide derivatives of this invention where $R_1$ is a 1-deoxy pentose moiety are shown below for arabinose:

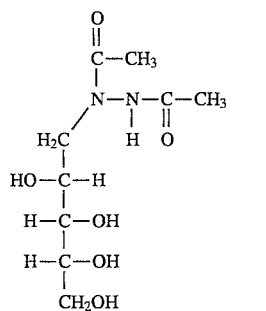
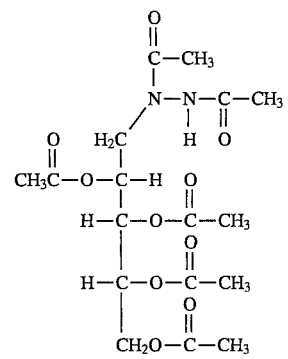

Representative examples of 1-deoxy hexose derivatives are shown below for glucose:

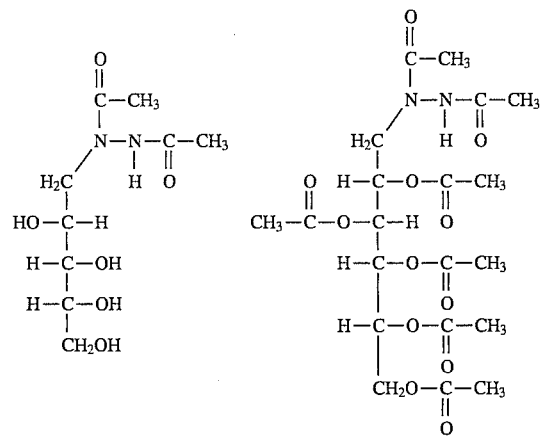

Representative examples of 2-deoxy hexose derivatives are shown below for D-fructose:

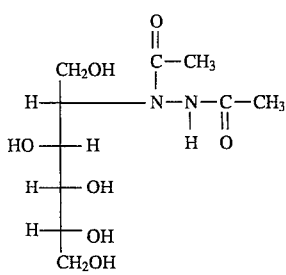

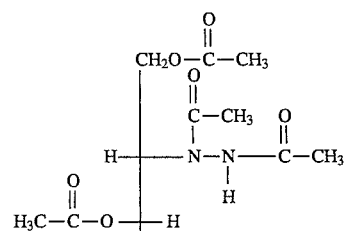

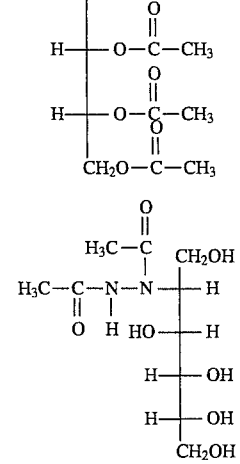

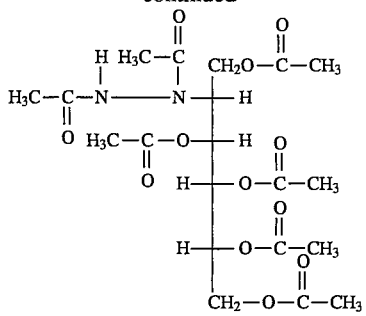

In another preferred embodiment, $R_1$ is derived from an aldose or a ketose that was originally located at the reducing end of an oligosaccharide.

$R_2$ is generally hydrogen or a linear or branched alkyl group. Preferably, $R_2$ is an alkyl group possessing from 1 to 8 carbon atoms. More preferably, $R_2$ is an alkyl group having from 1 to 6 carbon atoms.

The monosaccharide derivatives of this invention may generally be prepared by: (a) generating from a monosaccharide (either free or at the reducing end of an oligosaccharide) a hydrazone or alkylhydrazone derivative, (b) reducing that derivative to give a deoxy-hydrazinoalditol derivative or a deoxy-(N'-alkyl hydrazino) alditol derivative or (in the case of reducing oligosaccharides) such a derivative substituted with a glycosidic linkage, and (c) acetylating the reduced derivative, either only on the nitrogen atoms to give the deoxy-(N,N'-diacetylhydrazino) alditol or the deoxy-(N'-alkyl-N,N'-diacetylhydrazino) alditol, or on both free hydroxyl groups and nitrogen atoms to give the per-O-acetylated derivative of the deoxy-(N,N'-diacetylhydrazino) alditol or the deoxy-(N'-alkyl-N,N'-diacetylhydrazino) alditol derivative. Alternatively, the deoxy-(N,N'-diacetylhydrazino) alditol may be alkylated to give the deoxy-(N'-alkyl-N,N'-diacetylhydrazino) alditol or its partially or fully O-alkylated derivative. Regardless of the procedure used, 90–95% of the monosaccharide may be convened to the desired derivative.

For example, an aldose derivative may be formed by (a) generating a hydrazone or alkylhydrazone derivative, (b) reducing that derivative to give a 1-deoxy-1-hydrazino alditol or a 1-deoxy-1-(N'-alkylhydrazino) alditol, and (c) acetylating the reduced derivative to give the 1-deoxy-1-(N,N'-diacetylhydrazino) alditol, the 1-deoxy-1-(N'-alkyl-N,N'-diacetylhydrazino) alditol or a fully acetylated derivative thereof.

Similarly, a derivative of a ketose having a ketone group at C-2 may be formed by (a) generating a hydrazone or alkylhydrazone derivative, (b) reducing that derivative to give a 2-deoxy-2-hydrazino alditol or a 2-deoxy-2-(N'-alkylhydrazino) alditol, and (c) acetylating the reduced derivative to give the 2-deoxy-2-(N,N'-diacetylhydrazino) alditol, the 2-deoxy-2-(N'-alkyl-N,N'-diacetylhydrazino) alditol or a fully acetylated derivative thereof.

Derivatives of aldose and ketose monosaccharides present at the reducing end of an oligosaccharide may also be specifically generated by the method of this invention. Derivatives of internal monosaccharides are not generated because the carbonyl groups of those monosaccharides are involved in glycosidic linkages. Only the monosaccharide at the reducing end of the oligosaccharide contains a free carbonyl group, which is necessary for generating the hydrazone or alkylhydrazone derivative. Accordingly, the method of this invention may be used to selectively derivatize monosaccharides present at the reducing end of an oligosaccharide, and is thus useful for identifying those monosaccharides.

Where the derivatized monosaccharide is present at the reducing end of an oligosaccharide, the method of the present invention further comprises the step of cleaving the glycosidic linkages of the oligosaccharide. For example, the cleavage step may be accomplished using acidic conditions in various solvents such as water, alcohols, or carboxylic acids. Suitable cleavage reagents include hydrochloric acid or trifluoroacetic acid in water, hydrochloric acid in anhydrous methanol, and sulfuric acid in an anhydrous acetic acid solution. This cleavage is performed after the generation of the deoxy-hydrazinoalditol or deoxy-(N'-alkyl hydrazino) alditol derivative, so that only the reducing monosaccharide is derivatized. The cleavage may be performed before or after acetylation of the hydrazino derivative.

Briefly, to generate the hydrazone or alkylhydrazone derivative, any aldose or ketose may be reacted with a hydrazine derivative having the following structure:

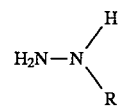

wherein R is hydrogen or a linear or branched alkyl group. Preferably, R is an alkyl group containing 1 to 8 carbon atoms and, more preferably, R is an alkyl group having 1 to 6 carbon atoms. The aldose or ketose may be a free monosaccharide or may be a monosaccharide at the reducing end of an oligosaccharide. The reaction between the aldose or ketose and the hydrazine derivative may be performed under appropriate conditions known to those in the art. Preferably, the reaction takes place over a period of from about 0.1 to 24 hours at room temperature.

In the hydrazone or alkylhydrazone derivative, the carbonyl oxygen atom of the aldose or ketose is replaced by a nitrogen atom of the hydrazine derivative. For example, a hydrazone derivative of D-glucose has the following structure:

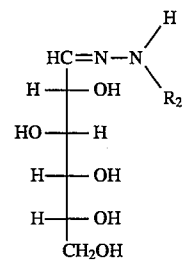

where $R_2$ is hydrogen or a linear or branched alkyl group.

The hydrazone or alkylhydrazone derivative may be reduced using any appropriate reducing agent known to those in the art, including, for example, borohydride reagents, such as sodium borohydride [these are available as a variety of salts, including cationic polymers in the borohydride form (for example, the polymer-supported borohydride reagents, products 32,864-2 and 35,994-7, Aldrich Chemical Co., Milwaukee, Wis.) and silica or alumina-supported sodium borohydride (products 24,361-2 and 24,362-0, Aldrich)]; boron-centered hydrides also having covalent boron-carbon linkages, such as alkyl, or bulky groups, or cyano groups bonded directly to boron [members of this class include potassium tri-sec-butylborohydride (K-selectride, Aldrich, product 22,076-0), KS-selectride, lithium 9-BBN hydride, L-selectride, L-S-selectride, R-Alpine-hydride, and S-Alpine-hydride (products 22,077-9, 34,423-0, 25,704-4, 22,592-4, 22,902-4, and 23,772-8, respectively, Aldrich Chemical Co., Milwaukee, Wis.)]; borane/diborane, often used as a complex with reagents such as triethylamine, diethylamine, t-butylamine, morpholine, pyridine, or tetrahydrofuran; aluminum hydride reagents, such as lithium aluminum hydride [these are available as other salts, such as sodium]; other aluminum-centered hydrides having covalently-linked carbons or alkoxy groups replacing hydrogens, such as diisobutylaluminum hydride [Aldrich, supplied as solutions in various solvents or sodium bis(2-methoxyethoxy) aluminum hydride (Red-Al, product 19,619-3, Aldrich Chemical Co., Milwaukee, Wis.)]. Catalytic hydrogenations may also be employed using hydrogen gas and various metals and prepared metal alloys, such as Raney nickel (a nickel-aluminum alloy). In addition, dissolving metal reductions, using alkali metals (lithium, sodium, or potassium), as well as, for example, zinc, magnesium, tin, iron, or mercury in solvents such as alcohols, acetic acid, liquid ammonia, or ethers such as 1,2-dimethoxyethane will generally be effective.

A preferred reducing agent is sodium borohydride. Reduction with sodium borohydride is generally conducted within a temperature range of from about 0° C. to about 100° C., with a temperature of from about 20° C. to about 40° C. being more typical. Preferably, the incubation of the hydrazone or alkylhydrazone derivative with reducing agent is performed for about 20 hours at room temperature, to yield the hydrazino or alkylhydrazino derivative. It will be appreciated by those of ordinary skill in the art that the time required for either of these reactions may be shortened or lengthened as the temperature is increased or decreased, respectively, from room temperature.

The reduction of the hydrazone generates a hydrazino derivative with the following structure:

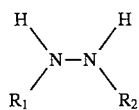

where $R_1$ is a 1-deoxy aldose moiety or a deoxy ketose moiety and $R_2$ is hydrogen or a linear or branched alkyl group.

The product and yield of the reduction step may be monitored by analytical techniques, such as proton NMR and mass spectrometry.

Following the reduction step, a hydrazino or alkylhydrazino monosaccharide derivative located at the reducing end of an oligosaccharide may be cleaved from the oligosaccharide. Any method of cleavage known to those in the art may be employed. Preferably, cleavage is achieved by 2.0M aqueous HCl for 3 hours at 100° C.

The hydrazino or alkylhydrazino derivative may be selectively acetylated to yield the deoxy-(N,N'-diacetylhydrazino) or deoxy-(N'-alkyl-N,N'-diacetylhydrazino) alditol derivative. Those of ordinary skill in the art will recognize that a variety of acetylation reactions will selectively acetylate the nitrogen atoms, while leaving the hydroxyl groups substantially unmodified. Selective N-acetylation may be carried out in an aqueous solution of saturated sodium bicarbonate with an excess of acetic anhydride. Ketene and acetyl halides, such as acetyl chloride, may also be used for selective N-acetylation reactions. In addition, the deoxy-(N,N'-diacetylhydrazino) alditol or deoxy-(N'-alkyl-N,N'-diacetylhydrazino) alditol derivatives may be generated by complete N- and O-acetylation as described below, followed by selective removal of the O-acetyl groups using, for example, sodium methoxide in methanol or ammonia in methanol. Preferably, the N-acetylation is achieved in saturated sodium bicarbonate with acetic anhydride for about 0.1 to 2 hours at a temperature of 0° C. to 60° C.

Oligosaccharides having a hydrazino or alkylhydrazino monosaccharide derivative located at the former reducing end may also be selectively N-acetylated as described above, giving derivatives having a deoxy-(N,N'-diacetylhydrazino) alditol or deoxy-(N'-alkyl-N,N'-diacetylhydrazino) alditol located at the former reducing end. Derivatization of these oligosaccharides causes them to absorb at ultraviolet wavelengths which may be useful for liquid chromatography. These derivatives can be cleaved from the oligosaccharide by any method known to those in the art. Preferably, 2.0M aqueous HCl for 3 hours at 100° C. is employed. These derivatives are converted to their respective hydrazino or alkylhydrazino monomers during the treatment, but can be selectively re-N-acetylated as described above, or fully N- and O-acetylated as described below. Like the oligosaccharides having a hydrazino or alkylhydrazino monosaccharide at the reducing end, the di-N-acetyl derivatives may be cleaved from the oligosaccharide and derivatized to enable the monosaccharide at the former reducing end of the oligosaccharide to be selectively and unambiguously identified as described below.

The end product of the monosaccharide derivatization may be the 1-deoxy-1-(N,N'-diacetylhydrazino) or 1-deoxy-1-(N'-alkyl-N,N'-diacetylhydrazino) alditol derivative. Alternatively, these derivatives may be further modified. For example, the derivatives may be fully acetylated prior to analysis. A fully acetylated derivative is one in which all of the free hydroxyl groups and nitrogen atoms are acetylated. Any appropriate O-acetylation reaction may be used to fully acetylate the derivative. These include, but are not limited to, reaction with acetic anhydride/pyridine mixtures, acetic anhydride and zinc chloride, sodium acetate, or sulfuric acid, or acetyl chloride in pyridine solution (see, e.g., Horton, D., IA, "The Amino Sugars," p. 3–211 (R. W. Jeanloz, ed., Academic Press, 1969)). Preferably, the acetylation is achieved by reaction with acetic anhydride in dry pyridine for about 12 to 24 hours.

N-acetylation occurs far more readily than O-acetylation. Consequently, complete N- and O-acetylation of the deoxyhydrazino alditols and deoxy-(N'-alkylhydrazino) alditols occurs under the conditions described above for "O-acetylation," giving rise to acetyl groups on both nitrogens and on all free hydroxyl groups of these molecules. These completely N- and O-acetylated molecules are fully acetylated.

An alternative method of generating the deoxy-(N'-alkyl-N,N'-diacetylhydrazino) alditol or its partially or fully O-alkylated derivative is the alkylation of the deoxy-(N,N'-diacetylhydrazino) alditol. Any appropriate alkylation procedure known to those in the art may be employed. For example, alkylation may be performed using an alkyl halide, such as methyl iodide, in a solvent such as dimethylsulfoxide, in the presence of a strong base such as sodium hydride. Those skilled in the art will recognize that O-alkylation may be prevented by blocking the free hydroxyl groups with a suitable blocking group prior to alkylation. Alternatively, the N- and O-alkylated derivative may be produced. In the case of oligosaccharides, alkylation may be performed before or after cleavage of the former reducing monosaccharide from the oligosaccharide.

The derivatives of this invention may be purified prior to analysis, but need not be purified prior to analyses that employ chromatographic separation coupled to on-line analyses, such as GCMS and LCMS. In the case of fully acetylated derivatives, the purification step may be performed before or after O-acetylation. Those of ordinary skill in the art will appreciate that any purification technique sufficient to remove N,N'-diacetylhydrazine or N-alkyl-N, N'-diacetylhydrazine from the derivatized monosaccharide may be employed. Preferably, the derivative is chromatographically purified and, more preferably, the purification is performed using high-performance liquid chromatography.

The purified N-acetylated or fully acetylated derivative may be used for structural determination of the monosaccharide. A preferred method of structural determination consists of chromatographic separation of the derivatized monosaccharide followed by analysis by mass spectrometry. More preferably, the separation is by gas chromatography. Gas chromatography may be carried out, for example, using a wide variety of capillary GC columns, using helium as a carrier gas, with temperature gradients in the range of 100° C. to 300° C. or under isothermal conditions in the same temperature range. The aldose derivatives of this invention elute in a single peak. Each ketose derivative will result in two characteristic peaks.

Detection of the derivative may be through any appropriate technique known to those in the art. Preferably, detection is performed using ultraviolet absorbance, typically at 200 nm, or mass spectrometry. Detection of the derivative using on-line mass spectrometry (i.e., the eluted compounds pass directly to the mass spectrometer for analysis) is particularly preferred. In mass spectral analysis, the total ion current may be monitored. The instrument may be used in the electron-impact mode or chemical ionization mode, using isobutane or other chemical ionization reagents. Mass spectrometry may be carried out on virtually any compound which is capable of forming stable ions. With many compounds, less than 1 pmol of compound can be analyzed by mass spectrometry. For on-line analyses (either LCMS, GCMS, or CZEMS), a quadrupole MS or ion trap MS is most suitable due to the ability to rapidly scan a sample over a reasonably broad mass range (approximately 1 to 2000 atomic mass units in less than one second). A review of the basic instrumentation has been published (Cooks, R. G., Glish, G. L., McLucky, S. A. and Kaiser, R. E., *Chemical and Engineering News*, Mar. 25, 1991, pp. 26–41). Instruments with on-line MS analysis permit molecules eluted from the gas chromatography column to be ionized by electron impact or chemical ionization. Typically, the electron impact mass spectra provide a mass spectrum which may be regarded as a "fingerprint" for a specific class of compounds. Chemical ionization leads to ionization with little breakdown of the molecule, so that major fragments of a molecule are maintained. Mass spectral analysis is particularly useful for identifying branched monosaccharides and distinguishing between classes of monosaccharides, permitting unambiguous assignment of monosaccharides when all members of a given class are chromatographically separable.

It will be evident to those of ordinary skill in the art that any or all of the various reaction steps described above may be performed under liquid phase or solid phase conditions. Typically in solid phase methodology, a reactant or reagent is immobilized on a solid support such as glass beads, polymeric matrices, scintered glass discs, fiberglass membranes, or polymeric membranes. For example, a hydrazine derivative may be covalently linked (e.g., directly or via a crosslinking agent) to a chromatography resin and a saccharide brought in contact with the resin under conditions and for a time sufficient to permit the reaction(s) to proceed. Alternatively, a saccharide may be immobilized and contacted with the various reactants in a step-wise manner with one or more wash steps interposed where desired.

It will also be apparent that the various reaction steps described above, whether performed under liquid phase or solid phase conditions, may be incorporated into a system which automates the reactions. Such a system is typically in an instrument format. A system may comprise multiple reaction vessels, where within each vessel a single chemical reaction is performed. In such a system, a saccharide is transported from vessel to vessel to accomplish the overall series of reactions. Alternatively, a system may be comprised of a single reaction vessel, where all the chemical reactions are performed step-wise by the sequential addition and removal of the appropriate reagents. In such a system, a saccharide may be immobilized within the reaction vessel and the necessary reagents for a particular reaction introduced under conditions and for a time sufficient to effect the reaction. Following completion of a reaction step, the reaction vessel is flushed to remove any reagents and by-products, leaving the immobilized, modified saccharide. A new set of reagents is introduced, reacted, and the removal process repeated to accomplish a second reaction step in a series of reactions. It will be evident to those of ordinary skill in the art that a variety of ways exist for automating the methods of the present invention.

To summarize the examples which follow, Example 1 describes the synthesis of fully acetylated hydrazino monosaccharide derivatives from free monosaccharides. Example 2 describes the synthesis of fully acetylated hydrazino monosaccharide derivatives from monosaccharides at the reducing end of an oligosaccharide. Example 3 describes the chromatographic purification of representative 1-deoxy-1-(N,N'-diacetylhydrazino) alditols. Example 4 describes the chromatographic separation of representative fully acetylated derivatives of this invention. Example 5 describes the analysis of representative fully acetylated 1-deoxy1-(N,N'-diacetylhydrazino) alditols using mass spectrometry.

The following examples are offered by way of illustration and not by way of limitation.

EXAMPLES

EXAMPLE 1

SYNTHESIS OF MONOSACCHARIDE DERIVATIVES FROM FREE MONOSACCHARIDES

This Example illustrates the synthesis of monosaccharide derivatives of this invention from free monosaccharides. The yield of the derivatives described below was greater than 95%.

A. 1-deoxy-1-hydrazino-D-glucitol heptaacetate

D-glucose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-glucitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-glucitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 42.5 minutes. For per-O-acetylation, 1.0 µmol of 1-deoxy-1-(N,N'-diacetylhydrazino)-D-glucitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the higher mass ion 448 becomes more abundant. (see, e.g., the inset of FIG. 7a). CIMS gave major ions at 491 $(MH)^+$, 449 $(MH-42)^+$ and 43 1 $(MH-60)^+$. These data show the generation of 1-deoxy-1-hydrazino-D-glucitol heptaacetate.

B. 1-deoxy-1-hydrazino-D-allitol heptaacetate

D-allose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-allose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-allitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-allitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 41 minutes. For per-O-acetylation, 1.0 µmol of 1-deoxy-1-(N,N'-diacetylhydrazino)-D-allitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-allitol heptaacetate.

C. 1-deoxy-1-hydrazino-D-altritol heptaacetate

D-altrose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-altrose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-altritol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-altritol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 42 minutes. For per-O-acetylation, 1.0 μmol of 1-deoxy-1-(N,N'-diacetylhydrazino)-D-altritol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-altritol heptaacetate.

D. 1-deoxy-1-hydrazino-D-galactitol heptaacetate

D-galactose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was convened to the hydrazone derivative of D-galactose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-galactitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-galactitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 45.5 minutes. For per-O-acetylation, 1.0 μmol of 1-deoxy-1-(N,N'-diacetylhydrazino)-D-galactitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-galctitol heptaacetate.

E. 1-deoxy-1-hydrazino-D-gulitol heptaacetate

D-gulose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-gulose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-gulitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-gulitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 42 minutes. For per-O-acetylation, 1.0 μmol of 1-deoxy-1-(N,N'-diacetylhydrazino)-D-gulitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-gulitol heptaacetate.

F. 1-deoxy-1-hydrazino-D-iditol heptaacetate

D-idose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-idose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-iditol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-iditol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 43 minutes. For per-O-acetylation, 1.0 µmol of 1-deoxy-1-(N,N'-diacetylhydrazino)-D-iditol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-iditol heptaacetate.

G. 1-deoxy-1-hydrazino-D-mannitol heptaacetate

D-mannose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-mannose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-mannitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-mannitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300mm), using isocratic acetonitrile/water, at 85/15, vol/vol, 1.0 mL/min, monitoring at a wavelength of 200 nm, giving a single sugar component as a single peak at 43.5 minutes. For per-O-acetylation, 1.0 µmol of 1-deoxy-1-(N,N'-diacetylhydrazino)-D-mannitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 448 ($M^+$-42), 431 ($M^+$-59), 195, 153, 141, 129, and 87, with a number of less abundant ions. With lower filament power, the ion at mass 448 becomes more abundant. CIMS gave major ions at 491 $(MH)^+$, 449 $(MH-42)^+$ and 431 $(MH-60)^+$. These data show the generation of 1-deoxy-1-hydrazino-D-mannitol heptaacetate.

H. 1-deoxy-1-hydrazino-D-talitol heptaacetate

D-talose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-talose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-talitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-talitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 42 minutes. For per-O-acetylation, 1.0 μmol of 1-deoxy-1-(N,N'-diacetylhydrazino)-D-talitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with major mass ions (EIMS) at 448 ($M^+$-42), 431 ($M^+$-59), 195, 153, 141, 129, and 87, with a number of less abundant ions. With lower filament power, the ion at mass 448 becomes more abundant CIMS gave major ions at 491 $(MH)^+$, 449 $(MH-42)^+$ and 431 $(MH-60)^+$. These data show the generation of 1-deoxy-1-hydrazino-D-talitol heptaacetate.

I. 1-deoxy-1-hydrazino-D-arabinitol hexaacetate

D-arabinose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-arabinose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-arabinitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-arabinitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 34 minutes. For per-O-acetylation, 1.0 μmol of 1-deoxy-1-(N,N'-diacetylhydrazino)-D-arabinitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (ELMS) at 376 ($M^+$-42), 359 ($M^+$-59), 196, 153, 141, 129, and 87, with a number of less abundant ions. With lower filament power, ions at 376, 129, and 87 were most abundant. These data show the generation of 1-deoxy-1-hydrazino-D-arabinitol hexaacetate.

J. 1-deoxy-1-hydrazino-D-lyxitol hexaacetate

D-lyxose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-lyxose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-lyxitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, H⁺ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-lyxitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 34 minutes. For per-O-acetylation, 1.0 µmol of 1-deoxy-1-(N,N'-diacetylhydrazino)-D-lyxitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 376 ($M^+$-42), 359 ($M^+$-59), 196, 153, 141, 129, and 87, with a number of less abundant ions. With lower filament power, ions at 376, 129, and 87 were most abundant. These data show the generation of 1-deoxy-1-hydrazino-D-lyxitol hexaacetate.

K. 1-deoxy-1-hydrazino-D-ribitol hexaacetate

D-ribose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-ribose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-ribitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, H⁺ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-ribitol. This sample contained some additional N,N'-diacetylhydrazine. It was either directly -peracetylated as described below, or it was chromatographically purified prior to -acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 33 minutes. For per-O-acetylation, 1.0 µmol of 1-deoxy-1-(N,N'-diacetylhydrazino)-D-ribitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 376 ($M^+$-42), 359 ($M^+$-59), 196, 153, 141, 129, and 87, with a number of less abundant ions. With lower filament power, ions at 376, 129, and 87 were most abundant. These data show the generation of 1-deoxy-1-hydrazino-D-ribitol hexaacetate.

L. 1-deoxy-1-hydrazino-D-xylitol hexaacetate

D-xylose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-xylose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-xylitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12mL of well-washed Dowex AG1-X8, 100–200 mesh, H⁺ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-xylitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 34 minutes. For per-O-acetylation, 1.0 µmol of 1-deoxy-1-(N,N'-diacetylhydrazino)-D-xylitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 376 ($M^+$-42), 359 ($M^+$-59), 196, 153, 141, 129, and 87, with a number of less abundant ions. With lower filament power, ions at 376, 129, and 87 were most abundant. These data show the generation of 1-deoxy-1-hydrazino-D-xylitol hexaacetate.

M. 2-amino-1,2-dideoxy-1-hydrazino-D-glucititol heptaacetate 2-amino-2-deoxy-D-glucose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 2-amino-2-deoxy-D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 2-amino-1,2-dideoxy-1-hydrazino-D-glucitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-amino-1-(N,N'-diacetylhydrazino)-1,2-dideoxy-D-glucitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 41 minutes. For per-O-acetylation, 1.0 µmol of 2-amino-1-(N,N'-diacetylhydrazino)-1,2-dideoxy-D-glucitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 374, 251, 209, 181, 139, 119, 96, 87, and 84, with a number of less abundant ions. CIMS gave major ions at 490 $(MH)^+$, 472 (MH-18), 448 $(MH-42)^+$ and 430 $(MH-60)^+$. These data show the generation of 2-amino-1,2-dideoxy-1-hydrazino-D-glucitol heptaacetate.

N. 2-amino-1,2-dideoxy-1-hydrazino-D-galactitol heptaacetate 2-amino-2-deoxy-D-galactose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 2-amino-2-deoxy-D-galactose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 2-amino-1,2-dideoxy-1-hydrazino-D-galactitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20mL methanol alone, to remove boric acid, thereby resulting in 2-amino-1-(N,N'-diacetylhydrazino)-1,2-dideoxy-D-galactitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 36.5 minutes. For per-O-acetylation, 1.0 µmol of 2-amino-1-(N,N'-diacetylhydrazino)-1,2-dideoxy-D-galactitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 374, 251, 209, 181, 139, 114, 96, 87 and 84, with a number of less abundant ions. CIMS gave major ions at 490 $(MH)^+$, 472 $(MH-18)^+$ 448 $(MH-42)^+$ and 430 $(MH-60)^+$. These data show the generation of 2-amino-1,2-dideoxy-1-hydrazino-D-galactitol heptaacetate.

O. 1,6-dideoxy-1-hydrazino-L-galactitol heptaacetate 6-deoxy-L-galactose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 6-deoxy-L-galactose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1,6-dideoxy-1-hydrazino-L-galactitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12mL of well-washed Dowex AG1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-(N,N'-diacetylhydrazino)-1,6-dideoxy-L-galactitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 nm, giving a single sugar component as a single peak at 28 minutes. For per-O-acetylation, 1.0 μmol of 1-(N,N'-diacetylhydrazino)-1,6-dideoxy-L-galactitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 390 ($M^+$-42), 373 ($M^+$-59), 141, 129, 100, and 87, with a number of less abundant ions. At lower filament power, ions at mass 390, 129, and 87 were most abundant. These data show the generation of 1,6-dideoxy-1-hydrazino-L-galactitol heptaacetate.

P. 1,6-dideoxy-1-hydrazino-L-mannitol heptaacetate 6-deoxy-L-mannose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was convened to the hydrazone derivative of 6-deoxy-L-mannose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1,6-dideoxy-1-hydrazino-L-mannitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-(N,N'-diacetylhydrazino)-1,6-dideoxy-L-mannitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, 1.0 mL/min, monitoring at a wavelength of 200 ran, giving a single sugar component as a single peak at 27.5 minutes. For per-O-acetylation, 1.0 μmol of 1-deoxy-1-(N,N'-diacetylhydrazino)-6-deoxy-L-mannitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar-derivative, with mass ions (EIMS) at 390 ($M^+$-42), 373 ($M^+$-59), 141, 129, 100, and 87, with a number of less abundant ions. At lower filament power, ions at 390, 129, and 87 were most abundant. These data show the generation of 1,6-dideoxy-1-hydrazino-L-mannitol heptaacetate.

Q. 1-deoxy-1-hydrazino-L-glucitol heptaacetate

L-glucose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of L-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-L-glucitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-L-glucitol. This sample contained some additional N,N'-diacetylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a single peak at 42.5 minutes. For per-O-acetylation, 1.0 μmol of 1-deoxy-1-(N,N'-diacetylhydrazino)-L-glucitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar derivative, with mass ions (EIMS) at 448 ($M^+$-42), 431 ($M^+$-59), 195, 153, 141, 129, and 87, with a number of less abundant ions. With lower filament power, the mass ion at 448 becomes more abundant. These data show that the product is 1-deoxy-1-hydrazino-L-glucitol heptaacetate.

R. 1-deoxy-1-hydrazino-3-O-methyl-D-glucitol hexaacetate

3-O-methyl-D-glucose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 3-O-methyl-D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-3-O-methyl-D-glucitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG 1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-3-O-methyl-D-glucitol. This sample contained some additional N,N'-diacetylhydrazine. It was either directly O-peracetylated on free hydroxyl groups as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a single peak at 31 minutes. For per-O-acetylation, 1.0 μmol of 1-deoxy-1-(N,N'-diacetylhydrazino)-3-O-methyl-D-glucitol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material derived from samples before or after HPLC purification by GCMS showed a single sugar derivative, with mass ions (EIMS) at 420 ($M^+$-42), 403 ($M^+$-59), 171, 143, 129, 125, and 87, with a number of less abundant ions. These data show that the product is 1-deoxy-1-hydrazino-3-O-methyl-D-glucitol hexaacetate.

S. 1-deoxy-1-hydrazino-D-threitol pentaacetate

D-threose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-threose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-threitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-threitol. This sample contained some additional N,N'-diacetylhydrazine. It was either directly -peracetylated as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a single peak at 27.5 minutes. For per-O-acetylation, 1.0 µmol of 1-deoxy-1-(N,N'-diacetylhydrazino)-D-threitol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed with a Speed-Vac rotary concentrator. The samples were solubilized in about 0.5 mL chloroform, and again concentrated on a Speed-Vac rotary concentrator. The samples were then taken up in 1.0 mL of chloroform for GCMS analysis, and were serially diluted for sensitivity studies. Analysis of the per-O-acetylated material by GCMS gave a sugar derivative with mass ions (EIMS) predominantly at 304 ($M^+$-42), 129, and 87, with low filament power. CIMS gave major ions at 347 $(MH)^+$, 305 $(MH-42)^+$, and 287 $(MH-60)^+$. These data show that the product is 1-deoxy-1-hydrazino-D-threitol pentaacetate.

T. 1-deoxy-1-hydrazino-D-erythritol pentaacetate

D-erythrose (approximately 0.100 mmol) was obtained from Sigma Chemical Company but was only about 75% pure, containing additional sugar impurities. The material was taken to a syrup and dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-erythrose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-erythritol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG 1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-erythritol as the major component. This sample contained some additional N,N'-diacetylhydrazine and sugar contaminants. It was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a peak at 26 minutes (about 75%), having a significant shoulder at 27 minutes. Consequently, the products were separated by high-performance liquid chromatography on a Shodex DC-613 column, (6.0×150 mm), using isocratic acetonitrile/water at 85/15, vol/vol, at 0.6 mL/min, monitoring at a wavelength of 200 nm, which gave two separated peaks at 15.5 minutes (1-deoxy-1-[N,N'-diacetylhydrazino]-D-erythritol, about 75%) and 17.5 minutes (unknown contaminant). For per-O-acetylation, approximately 1.0 µmol of 1-deoxy-1-(N,N'-diacetylhydrazino)-D-erythritol, was dried in a Pierce reacti-vial in a Speed-Vac rotary concentrator. The dried sample was taken up in 100 µL of dry pyridine (Pierce, silylation grade) and 50 µL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. The sample was then taken up in 1.0 mL of chloroform for GCMS analysis, and was serially diluted for sensitivity studies. Analysis of the per-O-acetylated material by GCMS gave a sugar derivative with mass ions (EIMS), predominantly at 304 ($M^+$-42), 129, and 87, with low filament power. CIMS gave major ions at 347 $(MH)^+$, 305 $(MH-42)^+$, and 287 $(MH-60)^+$. These data show that the product is 1-deoxy-1-hydrazino-D-erythritol pentaacetate.

U. 1-deoxy-1-hydrazino-D-glycerol tetraacetate

D-glyceraldehyde (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-glyceraldehyde which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-D-glycerol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG 1-XS, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-D-glycerol. This sample contained some additional N,N'-diacetylhydrazine. It was either directly O-peracetylated on free hydroxyl groups as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a single product peak at 21.5 minutes. For per-O-acetylation, 1.0 µmol of 1-deoxy-1-(N,N'-diacetylhydrazino)-D-glycerol, either before or after liquid chromatographic purification was dried in a Pierce reacti-vial in a Speed-Vac rotary concentrator. The dried samples were taken up in 100 µL of dry pyridine (Pierce, silylation grade) and 50 µL acetic anhydride was added. The samples were kept under argon for 24 hours at room temperature, whereupon the solvent was removed under a flow of nitrogen. The samples were solubilized in about 0.5 mL chloroform, and again concentrated under a flow of nitrogen. These data show that the product is 1-deoxy-1-hydrazino-D-glycerol-tetraacetate.

V. 2-hydrazinoethanol triacetate

Glycolaldehyde (0.100 mmol, in dimeric form) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of glycolaldehyde which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 2-hydrazinoethanol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-(N,N'-diacetylhydrazino)-ethanol. This sample contained some additional N,N'-diacetylhydrazine. It was either directly O-peracetylated on the free hydroxyl group as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a single product peak at 17 minutes. For O-acetylation, 1.0 μmol of 2-(N,N'-diacetylhydrazino)-ethanol, either before or after liquid chromatographic purification was dried in a Pierce reacti-vial in a Speed-Vac rotary concentrator. The dried samples were taken up in 100 μL of dry pyridine (Pierce, silylation grade) and 50 μL acetic anhydride was added. The samples were kept under argon for 24 hours at room temperature, whereupon the solvent was removed under a flow of nitrogen. The samples were solubilized in about 0.5 mL chloroform, and again concentrated under a flow of nitrogen. These data show that the product is 2-hydrazinoethanol triacetate.

W. 1-deoxy-1-(N'-methylhydrazino)-D-glucitol heptaacetate

D-glucose (0.100 mmol) was dissolved in 1.0 mL methylhydrazine (Aldrich Chemical company) in a Pierce reacti-vial, and capped under nitrogen with a cap having a Pierce Tuf-bond teflon-silicone seal. The sample, after sitting at room temperature for 16 hours, was converted to the methylhydrazone derivative of D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-(N'-methylhydrazino)-D-glucitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetyl-N'-methylhydrazino)-D-glucitol. This sample contained some additional N,N'-diacetyl-N-methylhydrazine. It was either directly O-peracetylated as described below, or it was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a product eluting at 32 minutes. For per-O-acetylation, 1.0 μmol of 1-deoxy-1-(N,N'-diacetyl-N'-methylhydrazino)-D-glucitol (1.0 μmol) was dried in a Pierce reacti-vial in a Speed-Vac rotary concentrator. The dried sample was taken up in 100 μL of dry pyridine (Pierce, silylation grade) and 50 μL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. The sample was then taken up in 20 μL of chloroform for fast-atom bombardment (FAB) MS analysis. Analysis of the per-O-acetylated material showed a single sugar derivative, with mass ions (FABMS) at 505 $(MH)^+$, 463 $(MH-42)^+$ and 445 $(MH-60)^+$ and upon addition of sodium ion, 527 $(M+Na)^+$. These data show that the product is 1-deoxy-1-(N'-methylhydrazino)-D-glucitol heptaacetate.

X. 2-deoxy-2-hydrazino-D-gulitol heptaacetate and 2-deoxy-2-hydrazino-D-iditol heptaacetate D-sorbose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was convened to the hydrazone derivative of D-sorbose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to a mixture of 2-deoxy-2-hydrazino-D-gulitol and 2-deoxy-2-hydrazino-D-iditol. After 4 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-deoxy-2-(N,N'-diacetylhydrazino)-D-gulitol and its C-2 epimer 2-deoxy-2-(N,N'-diacetylhydrazino)-D-iditol. This sample contained some additional N,N'-diacetylhydrazine. It was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving a somewhat broad product peak at 34 minutes which contained both epimers. FABMS of this sample gave a molecular ion at 281 $(MH)^+$, and, upon addition of sodium ions, 303 $(M+Na)^+$. For per-O-acetylation, 1.0 μmol of this purified mixture of 2-deoxy-2-(N,N'-diacetylhydrazino)-D-gulitol and 2-deoxy-2-(N,N'-diacetylhydrazino)-D-iditol was dried in a Pierce reacti-vial in a Speed-Vac rotary concentrator. The dried sample was taken up in 100 μL of dry pyridine (Pierce, silylation grade) and 50 μL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. The sample was then taken up in 20 μL of chloroform for FABMS analysis, which showed the per-O-acetylated products, with mass ions at 491 $(MH)^+$, 449 $(MH-42)^+$, and 431 $(MH-60)^+$, and, in the presence of sodium ions, 513 $(M+Na)^+$. These data show that the products are 2-deoxy-2-hydrazino-D-gulitol heptaacetate and 2-deoxy-2-hydrazino-D-iditol heptaacetate.

Y. 2-deoxy-2-hydrazino-D-glucitol heptaacetate and 2-deoxy-2-hydrazino-D-mannitol heptaacetate D-fructose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-fructose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to a mixture of 2-deoxy-2-hydrazino-D-glucitol and 2-deoxy-2-hydrazino-D-mannitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, $H^+$ :form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-deoxy-2-(N,N'-diacetylhydrazino)-D-glucitol and its C-2 epimer 2-deoxy-2-(N,N'-diacetylhydrazino)-D-mannitol. This sample contained some additional N,N'-diacetylhydrazine. It was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving product peaks at 33 minutes and 36 minutes in relative quantities of 60/40, respectively. For per-O-acetylation, 1.0 μmol of a mixture of 2-deoxy-2-(N,N'-diacetylhydrazino)-D-glucitol and 2-deoxy-2-(N,N'-diacetylhydrazino)-D-mannitol was dried in a Pierce reacti-vial in a Speed-Vac rotary concentrator. The dried sample was taken up in 100 μL of dry pyridine (Pierce, silylation grade) and 50 μL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. These data show that the products are 2-deoxy-2-hydrazino-D-glucitol heptaacetate, and 2-deoxy-2-hydrazino-D-mannitol heptaacetate.

Z. 2-deoxy-2-hydrazino-D-galactitol heptaacetate and 2-deoxy-2-hydrazino-D-talitol heptaacetate D-tagatose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-tagatose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to a mixture of 2-deoxy-2-hydrazino-D-galactitol and 2-deoxy-2-hydrazino-D-talitol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, $H^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-deoxy-2-(N,N'-diacetylhydrazino)-D-galactitol and its C-2 epimer 2-deoxy-2-(N,N'-diacetylhydrazino)-D-talitol. This sample contained some additional N,N'-diacetylhydrazine. It was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving product peaks at 32 minutes and 35 minutes in relative quantities of 30/70, respectively. For per-O-acetylation, 1.0 μmol of a mixture of 2-deoxy-2-(N,N'-diacetylhydrazino)-D-galactitol and 2-deoxy-2-(N,N'-diacetylhydrazino)-D-talitol was dried in a Pierce reacti-vial in a Speed-Vac rotary concentrator. The dried sample was taken up in 100 μL of dry pyridine (Pierce, silylation grade) and 50 μL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. These data show that the products are 2-deoxy-2-hydrazino-D-galactitol heptaacetate, and 2-deoxy-2-hydrazino-D-talitol heptaacetate.

AA. 2-deoxy-2-hydrazino-D-allitol heptaacetate and 2-deoxy-2-hydrazino-D-altritol heptaacetate D-psicose (0.100 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of D-psicose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to a mixture of 2-deoxy-2-hydrazino-D-allitol and 2-deoxy-2-hydrazino-D-altritol. After 24 hours, the sample was placed in an ice-water bath and 0.200 mL of glacial acetic acid was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-XS, 100–200 mesh, H+ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-deoxy-2-(N,N'-diacetylhydrazino)-D-allitol and its C-2 epimer 2-deoxy-2-(N,N'-diacetylhydrazino)-D-altritol. This sample contained some additional N,N'-diacetylhydrazine. It was chromatographically purified prior to O-acetylation by high-performance liquid chromatography on a Waters GlycoPak N column (7.8×300 mm), using isocratic acetonitrile/water, at 85/15, vol/vol, at 1.0 mL/min, monitoring at a wavelength of 200 nm, giving product peaks at 31 minutes and 33 minutes in relative quantities of 20/80, respectively. For per-O-acetylation, 1.0 µmol of a mixture of 2-deoxy-2-(N,N'-diacetylhydrazino)-D-allitol and 2-deoxy-2-(N,N'-diacetylhydrazino)-D-altritol was dried in a Pierce reacti-vial in a Speed-Vac rotary concentrator. The dried sample was taken up in 100 µL of dry pyridine (Pierce, silylation grade) and 50 µL acetic anhydride was added. The sample was kept under argon for 24 hours at room temperature, whereupon the solvent was removed with a Speed-Vac rotary concentrator. The sample was solubilized in about 0.5 mL chloroform, and again concentrated on a Speed-Vac rotary concentrator. These data show that the products are 2-deoxy-2-hydrazino-D-allitol heptaacetate, and 2-deoxy-2-hydrazino-D-altritol heptaacetate.

EXAMPLE 2

SYNTHESIS OF DIACETYLHYDRAZINO MONOSACCHARIDE DERIVATIVES FROM MONOSACCHARIDES AT THE REDUCING END OF OLIGOSACCHARIDES AND SUBSEQUENT IDENTIFICATION OF THE REDUCING MONOSACCHARIDE DERIVATIVE

This Example illustrates the synthesis of monosaccharide derivatives of this invention from monosaccharides present at the reducing end of an oligosaccharide. The yield of each of the derivatives described below was greater than 95%.

A. Preparation of 1-deoxy-1-hydrazino-D-glucitol heptaacetate from 4-0-β-D-galactopyranosyl-D-glucose and identification of the reducing monosaccharide 4-0-β-D-galactopyranosyl-D-glucose (0.050 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 4-0-β-D-galactopyranosyl-D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1 hydrazino-4-0-β-D-galactopyranosyl-D-glucitol. After 24 hours, the sample was placed in an ice-water bath and 0.200 mL of glacial acetic was added, dropwise, over about a 30 second interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and, after an additional 50 minutes, the sample was diluted with 5.0 mL water and loaded on a column containing 10–12 mL of well-washed Dowex AG1-X8, 100–200 mesh, H+ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-4-0-β-D-galactopyranosyl-D-glucitol.

This sample contained some additional N,N'-diacetylhydrazine, which was removed by purification of the sugar derivative by high-performance liquid chromatography on a Waters GlycoPak N column (7.8×300 mm), using isocratic acetonitrile/water, at 79/21, vol/vol, 1.0 mL/min, monitoring at a wavelength of 200 nm, giving a single sugar component as a single peak at 41 minutes.

The product, 1-deoxy-1-(N,N'-diacetylhydrazino)-4-0-β-D-galactopyranosyl-D-glucitol (1.0 µmol), was hydrolyzed, either before or after chromatographic purification, in 1.0 mL of 2.0M HCl for 3 hours at 100° C. in a vial, sealed under nitrogen. It was removed and rotary evaporated to dryness, then transferred to a small vial and concentrated to dryness. The remaining material was taken up in 50 µL acetic anhydride, followed immediately thereafter with 100 µL pyridine. After 16-24 hours at room temperature under nitrogen, the sample was concentrated on a Speed Vac rotary concentrator, followed by a wash with about 0.5 mL chloroform. The material was taken up in 1.0 mL chloroform and analyzed by GCMS. The per-O-acetylated product so obtained was identified as 1-deoxy-1-hydrazino-D-glucitol heptaacetate, based on its chromatographic comigration with the authentic compound and EIMS ions at 448 (M$^+$-42), 129, and 87, with low filament power.

B. Preparation of 1-deoxy-1-hydrazino-D-arabinitol hexaacetate from 3-0-β-D-galactopyranosyl-D-arabinose and identification of the reducing monosaccharide 3-0-β-D-galactopyranosyl-D-arabinose (0.50 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 3-O-β-D-galactopyranosyl-D-arabinose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 1-deoxy-1-hydrazino-3-O-β-D-galactopyranosyl-D-arabinitol. After 24 hours, the sample was placed in an ice-water bath and 0.200 mL of glacial acetic acid was added, dropwise, over about a 30 sec interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and after an additional 50 minutes, the sample was diluted with 5.0 mL water and 10–12 mL of well-washed Dowex AG1-X8, 100–200 mesh, H$^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 1-deoxy-1-(N,N'-diacetylhydrazino)-3-O-β-D-galactopyranosyl-D-arabinitol.

This sample contained some additional N,N'-diacetylhydrazine, which was removed by purification of the sugar derivative by high-performance liquid chromatography on a Waters GlycoPak N column (7.8×300 mm), using isocratic acetonitrile/water, at 79/21, vol/vol, 1.0 mL/min, monitoring at a wavelength of 200 nm, giving a single sugar component as a single peak at 37.5 minutes.

The product, 1-deoxy-1-(N,N'-diacetylhydrazino)-3-O-β-D-galactopyranosyl-D-arabinitol (1.0 µmol), was hydrolyzed, either before or after chromatographic purification, in 1.0 mL of 2.0M HCl for 3 hours at 100° C. in a vial, sealed under nitrogen. It was removed and rotary evaporated to dryness, then transferred to a small vial and concentrated to dryness. The remaining material was taken up in 50 µL acetic anhydride, followed immediately thereafter with 100 µL pyridine. After 16–24 hours at room temperature under nitrogen, the sample was concentrated on a Speed Vac rotary concentrator, followed by a wash with about 0.5 mL chloroform. The material was taken up in 1.0 mL chloroform and analyzed by GCMS. The per-O-acetylated product so obtained was identified as 1-deoxy-1-hydrazino-D-arabinitol hexaacetate, based on its chromatographic comigration with the authentic compound and EIMS ions at 376 (M$^+$-42), 129 and 87, with low filament power.

C. Preparation of 2-amino-1,2-dideoxy-1-hydrazino-D-glucitol heptaacetate from 2-acetamido-2-deoxy-4-O-β-D-galactopyranosy-D-glucose and identification of the reducing monosaccharide 2-acetamido-2-deoxy-4-O-β-D-galactopyranosyl-D-glucose (0.355 mmol) was dissolved in 1.0 mL anhydrous hydrazine (Pierce or Aldrich Chemical Company) in a Pierce reacti-vial, and capped under nitrogen with a cap having a Pierce Tuf-bond teflon-silicone seal. The sample, after sitting at room temperature for 16 hours, was converted to the hydrazone derivative of 2-acetamido-2-deoxy-4-O-β-D-galactopyranosyl-D-glucose which was evaporated to a resin-like material in a Speed-Vac concentrator. The sample was quantitatively transferred in a 1.0 mL volume of water into a 20 mL test tube, and 100 mg of sodium borohydride was added, which reduced the molecule to 2-acetamido-1,2-dideoxy-1-hydrazino-4-O-β-D-galactopyranosyl-D-glucitol. After 24 hours, the sample was placed in an ice-water bath and 0.200 mL of glacial acetic acid was added, dropwise, over about a 30 sec interval. The sample was diluted with 1.0 mL water. To it was added 200 mg of sodium bicarbonate and the bicarbonate was permitted to dissolve, with occasional mixing. Then, 0.100 mL acetic anhydride was added, followed by gentle swirling to dissolve all of it. After 10 minutes, another 0.100 mL acetic anhydride was added, the solution gently swirled to dissolve it, and after an additional 50 minutes, the sample was diluted with 5.0 mL water and 10–12 mL of well-washed Dowex AG1-XS, 100–200 mesh, H$^+$ form, to remove sodium. The column was washed with five additional washes of 10 mL water. The total eluate was rotary evaporated to near dryness, and then rotary evaporated to dryness five times with 20 mL of 1% acetic acid in methanol, and three times with 20 mL methanol alone, to remove boric acid, thereby resulting in 2-acetamido-1,2-dideoxy-1-(N,N'-diacetylhydrazino)-4-O-β-D-galactopyranosyl-D-glucitol.

This sample contained some additional N,N'-diacetylhydrazine, which was removed by purification of the sugar derivative by high-performance liquid chromatography on a Waters GlycoPak N column (7.8×300 mm), using isocratic acetonitrile/water, at 79/21, vol/vol, 1.0 mL/min, monitoring at a wavelength of 200 nm, giving a major sugar component as a peak at 35 minutes.

The product, 2-acetamido-1,2-dideoxy-1-(N,N'-diacetylhydrazino)-4-O-β-D-galactopyranosyl-D-glucitol (1.0 µmol), was hydrolyzed, either before or after chromatographic purification, in 1.0 mL of 2.0M HCl for 3 hours at 100° C. in a vial, sealed under nitrogen. It was removed and rotary evaporated to dryness, then transferred to a small vial and concentrated to dryness. The remaining material was taken up in 50 µL acetic anhydride, followed immediately thereafter with 100 µL pyridine. After 16–24 hours at room temperature under nitrogen, the sample was concentrated on a Speed Vac rotary concentrator, followed by a wash with about 0.5 mL chloroform. The material was taken up in 1.0 mL chloroform and analyzed by GCMS. The per-O-acetylated product so obtained was identified as 2-amino-1,2-dideoxy-1-hydrazino-D-glucitol heptaacetate, based on its chromatographic comigration with the authentic compound and EIMS ions at 374, 251, 181, 139, 114, 96, 87, and 84.

EXAMPLE 3

PURIFICATION OF N-ACETYLATED DERIVATIVES

N-acetylated monosaccharide derivatives were generally purified by dissolving in 85% acetonitrile, 15% water, with isocratic chromatography using an HPLC column (Waters, Glyco Pak N, 7.8×300 mm) with 85% acetonitrile, 15% water, at a flow rate of 1.0 mL/minute. Oligosaccharides derivatized at the former reducing monosaccharide are also purified on the same column using acetonitrile/water volume ratios ranging from 65/35 to about 80/20. Ultraviolet light absorbance was monitored at a wavelength of 200 nm. Under these conditions, a major contaminating product (N,N'-diacetyl hydrazine) was found to elute after nearly 20 minutes, whereas the derivatized monosaccharides eluted at 5 later times.

FIGS. 5a–g show elution profiles of some 1-deoxy-1-(N,N'-diacetylhydrazino) alditols representative of specific classes of monosaccharides: for trioses (FIG. 5a), the derivative of D-glyceraldehyde; for tetroses (FIG. 5b), the derivative of D-threose; for pentoses (FIG. 5C), the derivative of D-xylose; for hexoses (FIG. 5d), the derivative of D-glucose; for amino sugars (FIG. 5e), the N-acetylated derivative of 2-amino-2-deoxy-D-galactose; for deoxy sugars, (FIG. 5f), the derivative of 6-deoxy-L-galactose (L-fucose); for sugars having one or more alkoxy ether substituents (FIG. 5g), the derivative of 3-O-methyl-D-glucose. In each figure, the first major peak (at almost 20 minutes) corresponds to the N,N'-diacetyl hydrazine and the second major peak (marked with an asterisk) corresponds to the derivative.

EXAMPLE 4

CHROMATOGRAPHIC SEPARATION OF FULLY ACETYLATED DERIVATIVES

Separations were performed either on a Hewlett-Packard 5890 GC or a Varian gas chromatograph, interfaced to an Extrel ELQ 400 MS, or a Finnigan MAT magnum mass spectrometer, respectively. The carrier gas was helium. Detection was performed using mass spectrometry, normally using total ion current monitoring in the electron-impact mode or chemical ionization mode.

Figure 6A:
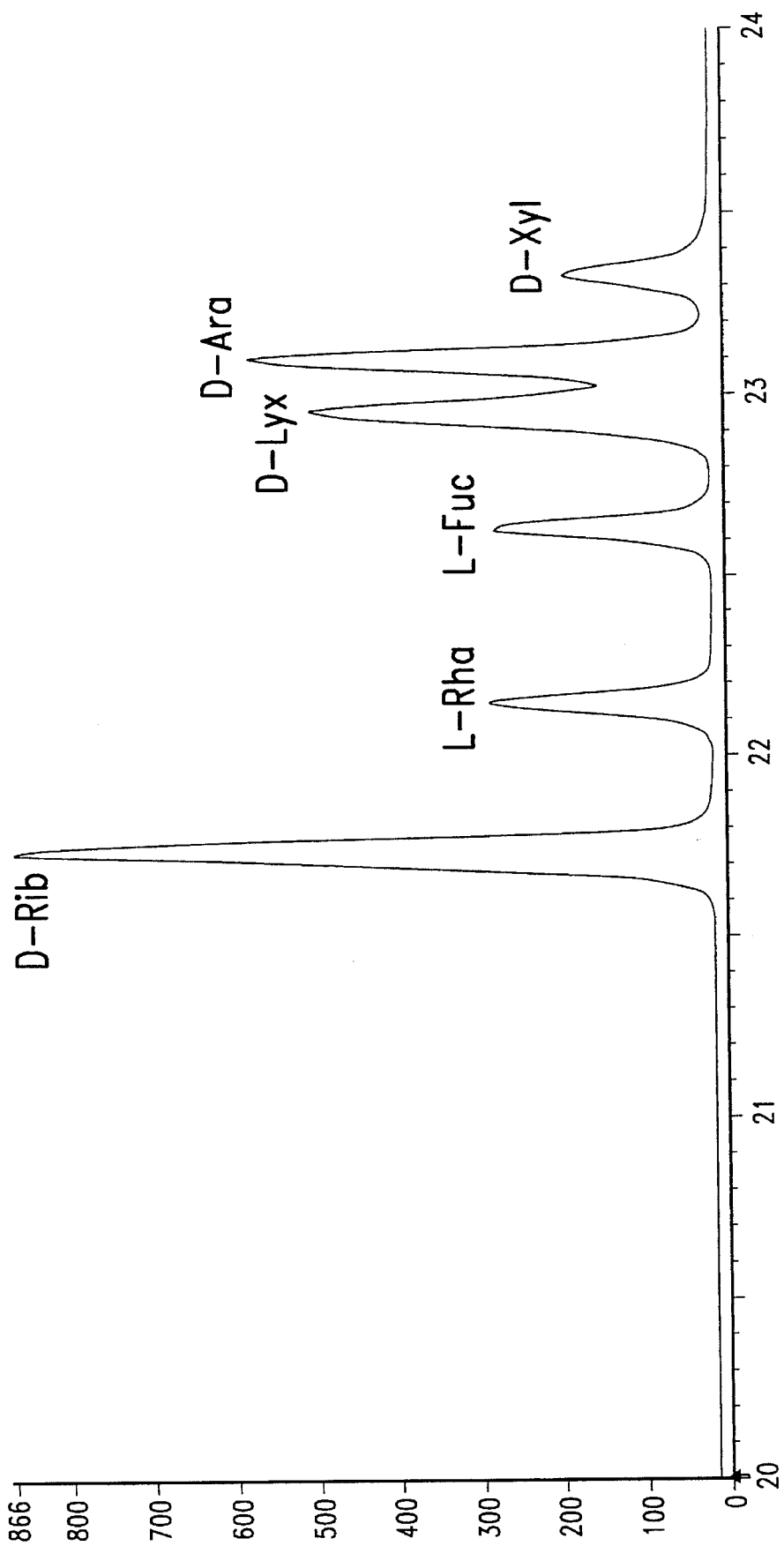
FIGS. 6a–d illustrate chromatographic separations of fully acetylated derivatives.
Figure 6B:
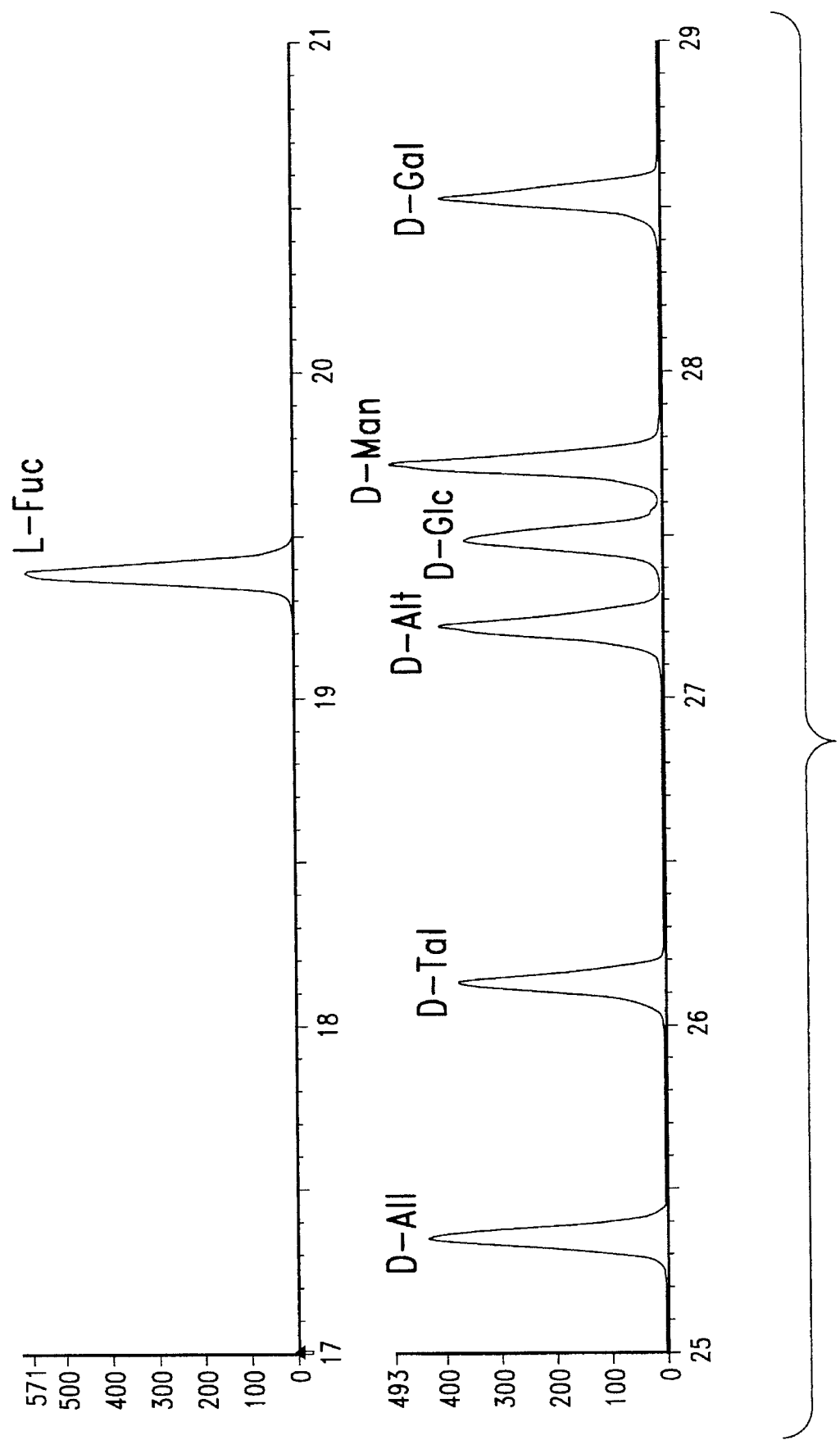
Figure 6C:
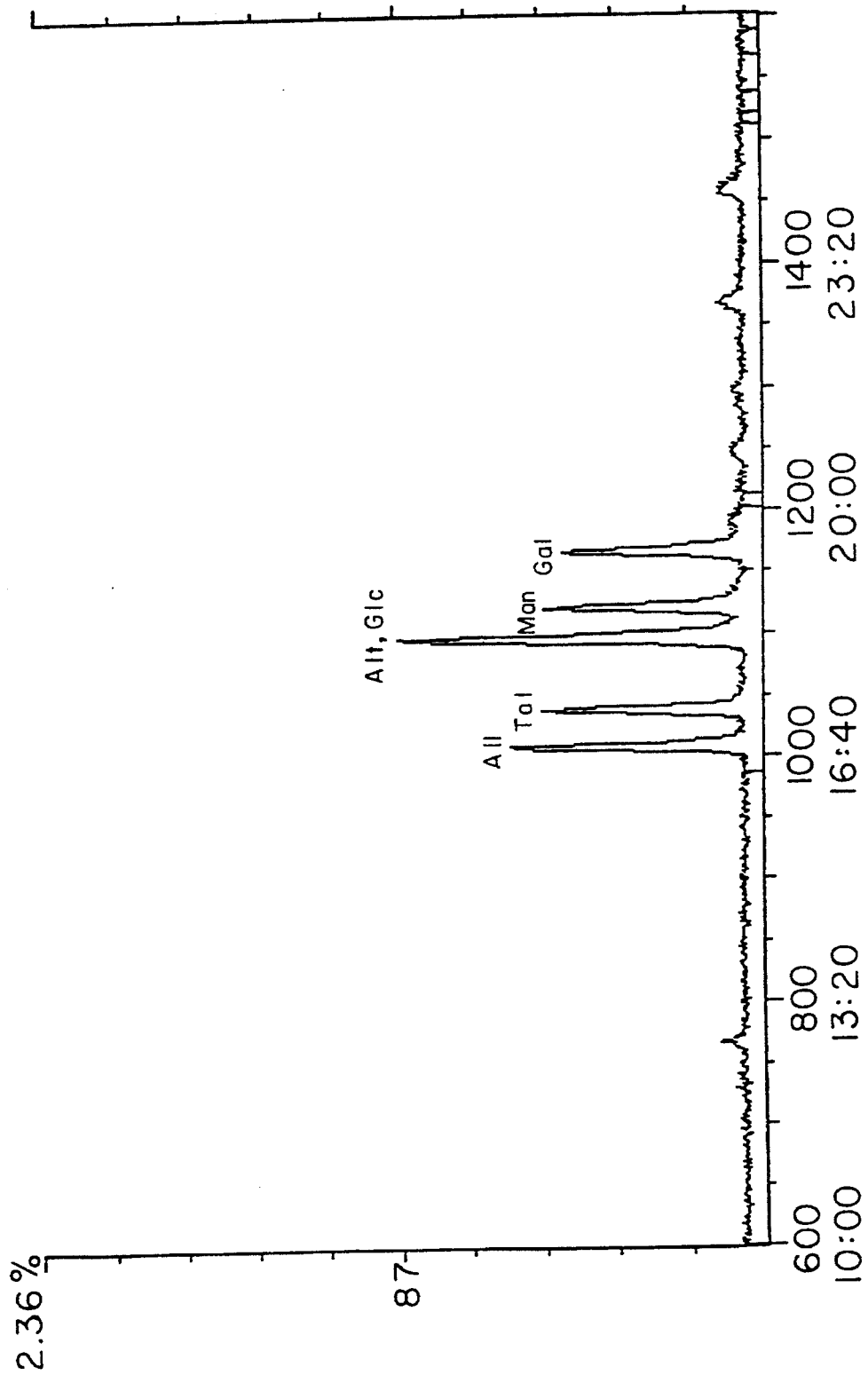
Figure 6D:
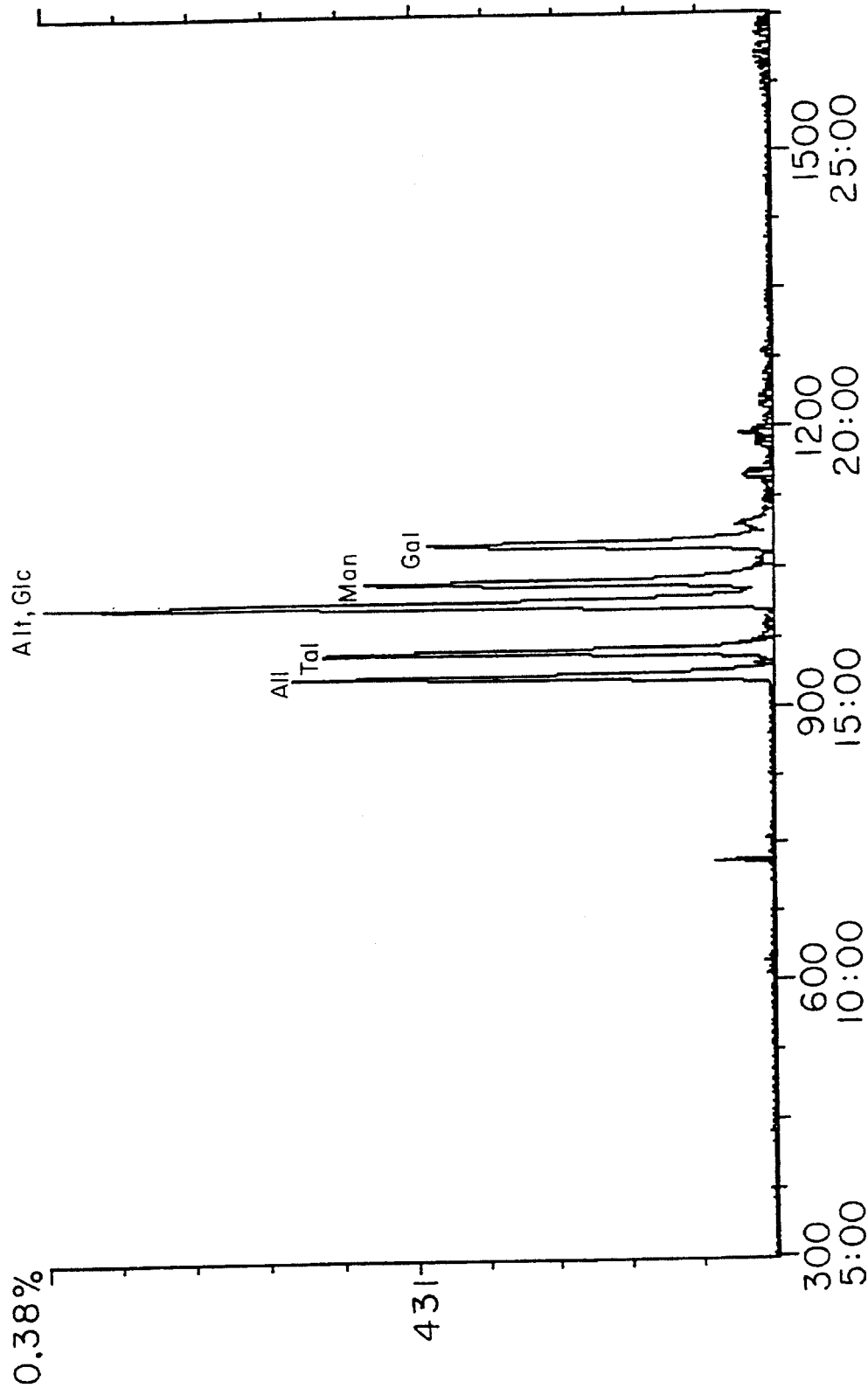

Shown in FIGS. 6a–d are some chromatographic separations performed with the fully acetylated derivatives: FIG. 6a shows the separation of about 50 μmol of four D-pentoses and two 6-deoxyhexoses (D-ribose, D-lyxose, D-arabinose, D-xylose, L-fucose and L-rhamnose), where the detection was performed using total ion current monitoring. FIG. 6b shows the separation of about 50 pmol of one 6-deoxy hexose (L-fucose) and six hexoses (D-allose, D-talose, D-altrose, D-glucose, D-mannose, and D-galactose), where the detection was performed using total ion current monitoring. In FIG. 6c, the same D-hexoses at the level of one picomole each were separated and detected using mass spectrometry in the electron impact mode. Finally, FIG. 6d shows the separation of the same D-hexoses at the level of one picomole each detected by mass spectrometry in the chemical ionization mode using isobutane.

EXAMPLE 5

MASS SPECTRAL ANALYSIS OF FULLY ACETYLATED DERIVATIVES

Figure 7A:
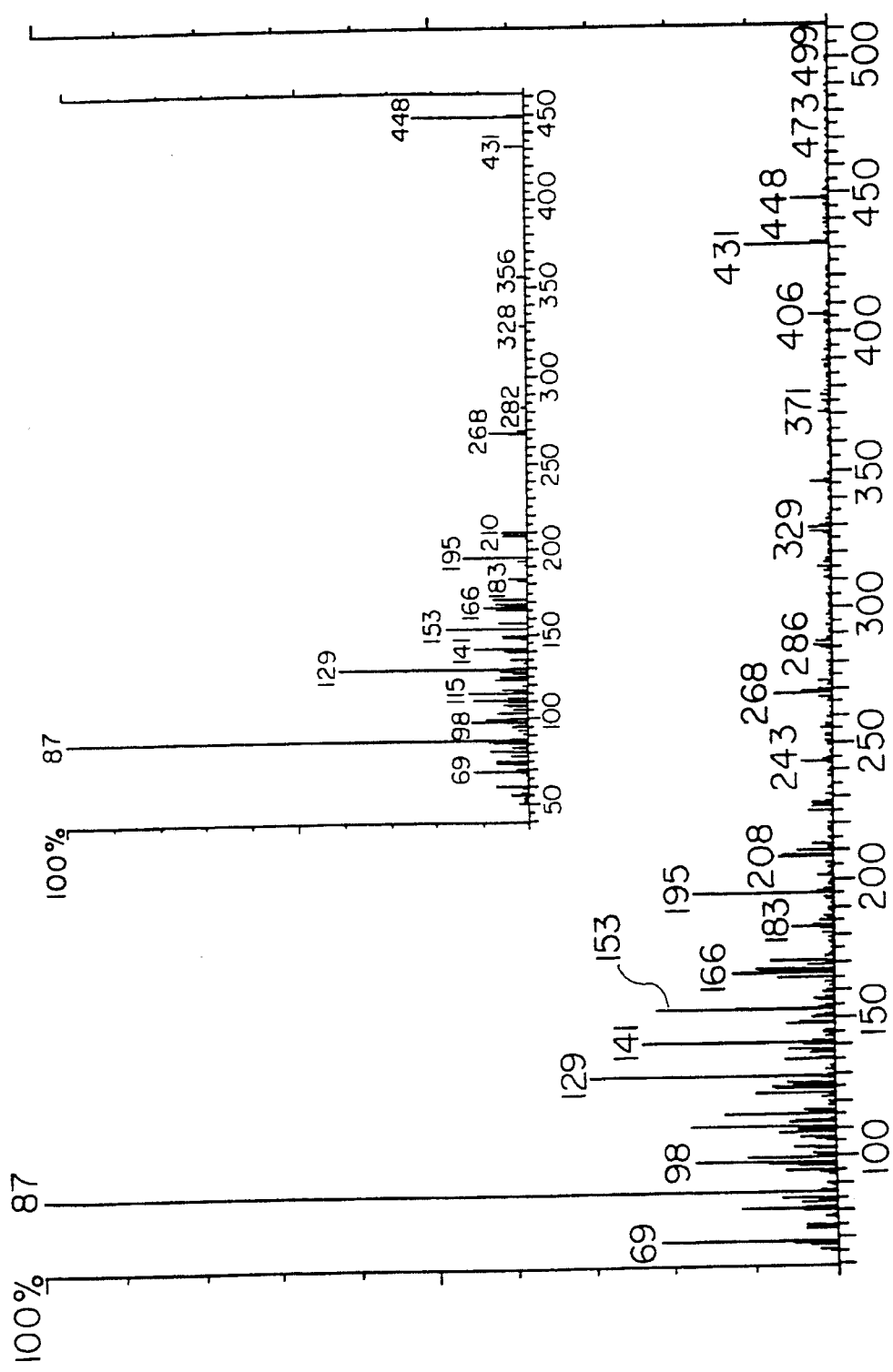
FIGS. 7a–e illustrate representative electron impact mass spectra of fully acetylated 1-deoxy-1-(N,N'-diacetylhydrazino) alditols.
Figure 7B:
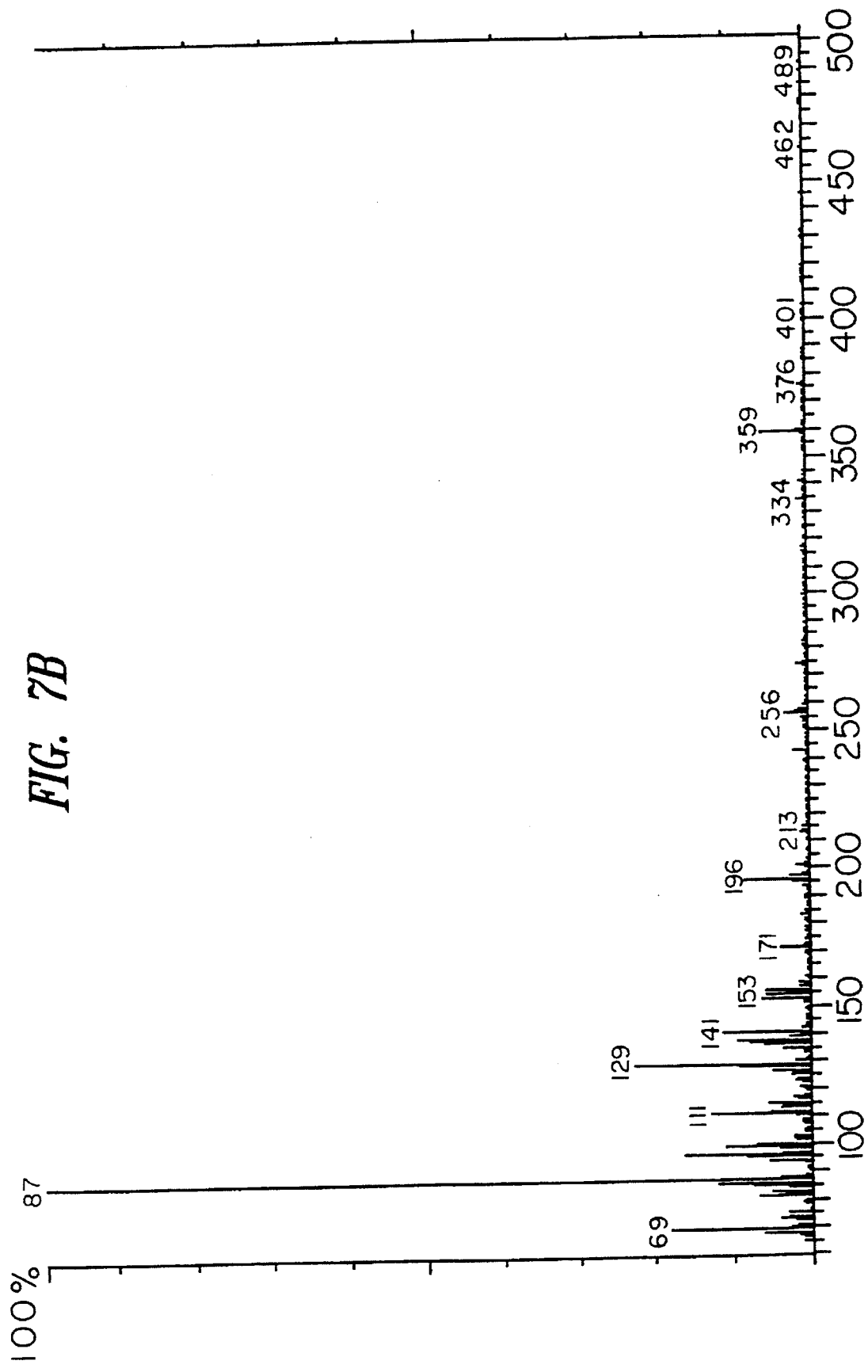
Figure 7C:
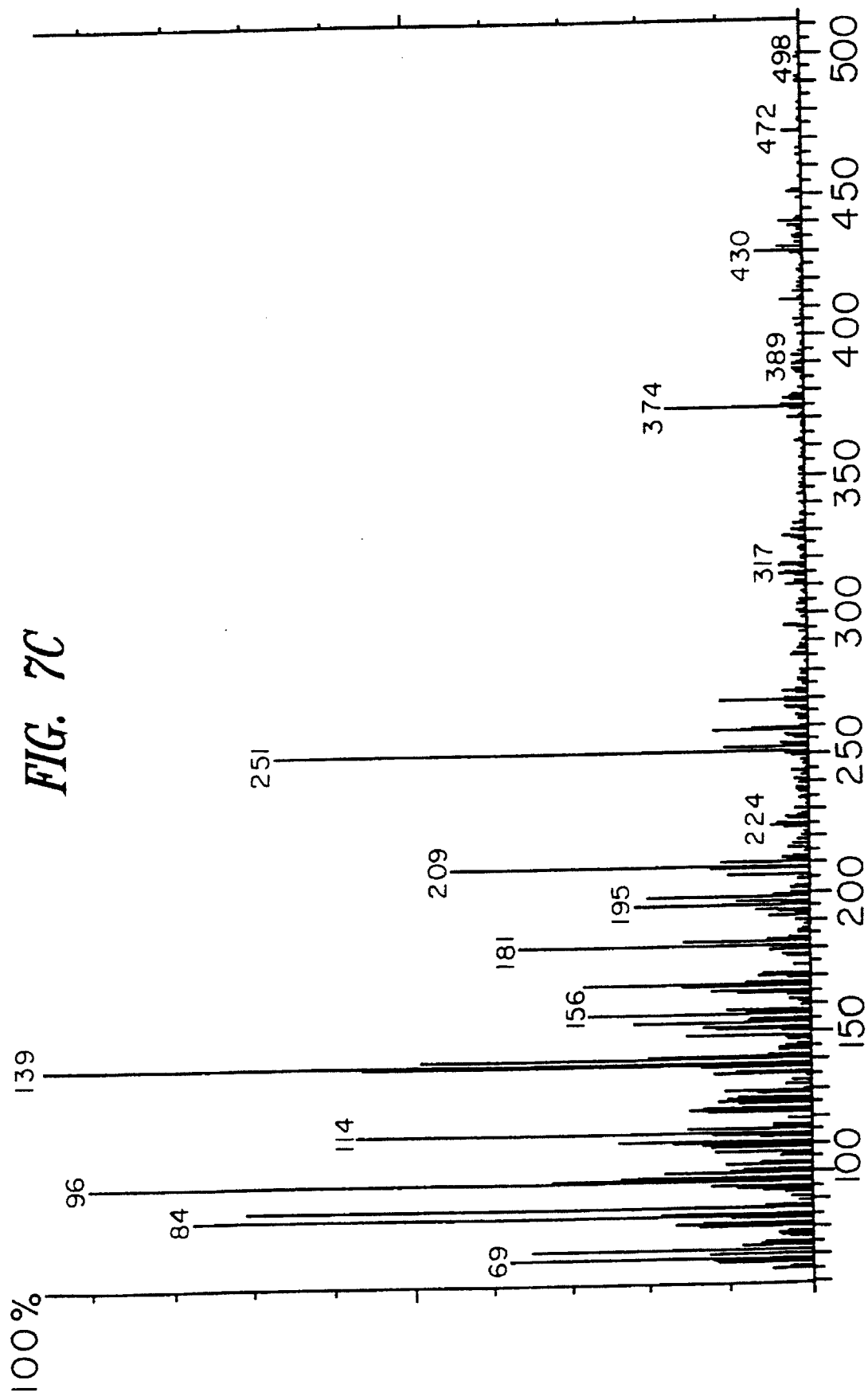
Figure 7D:
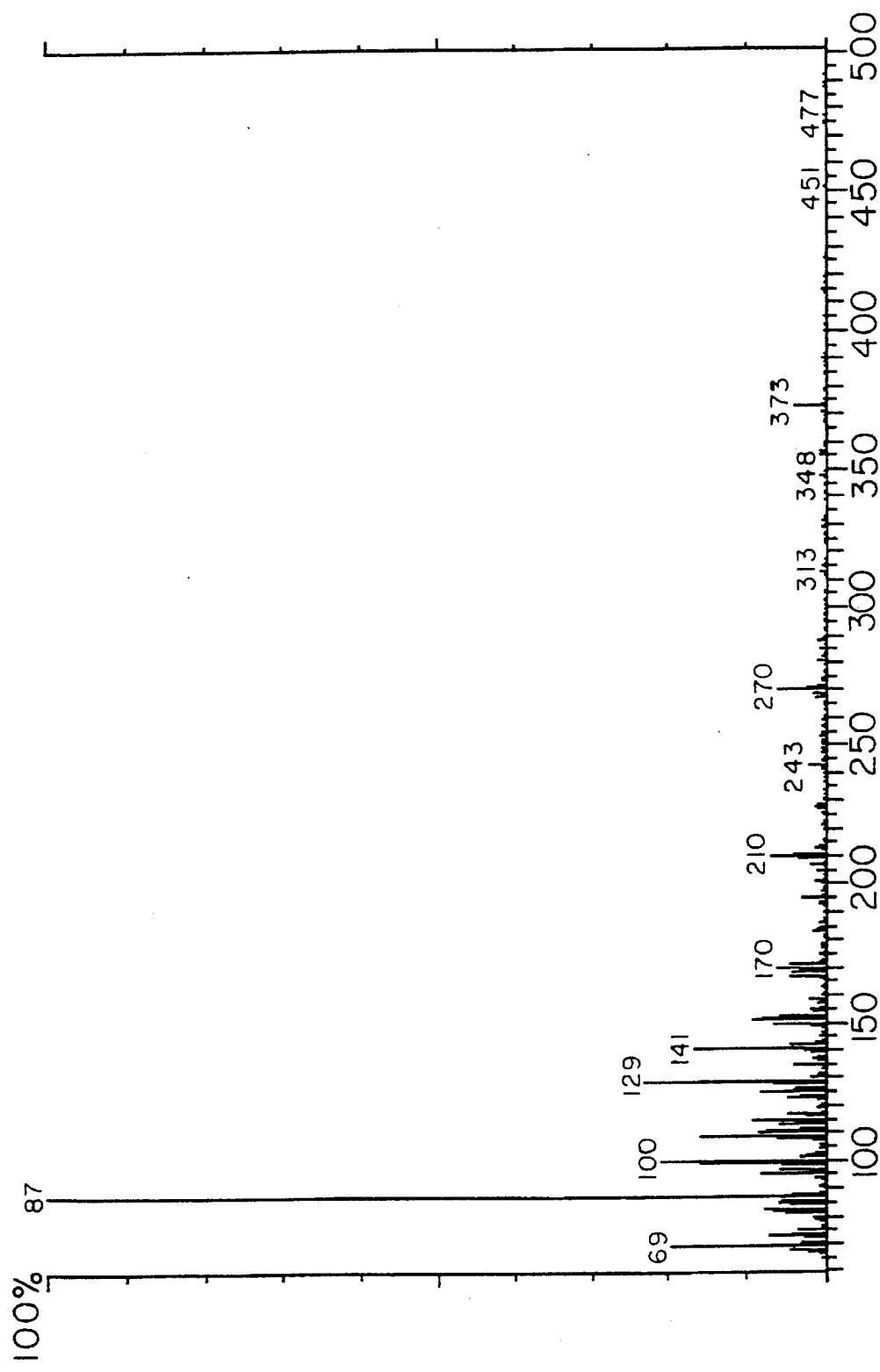
Figure 7E:
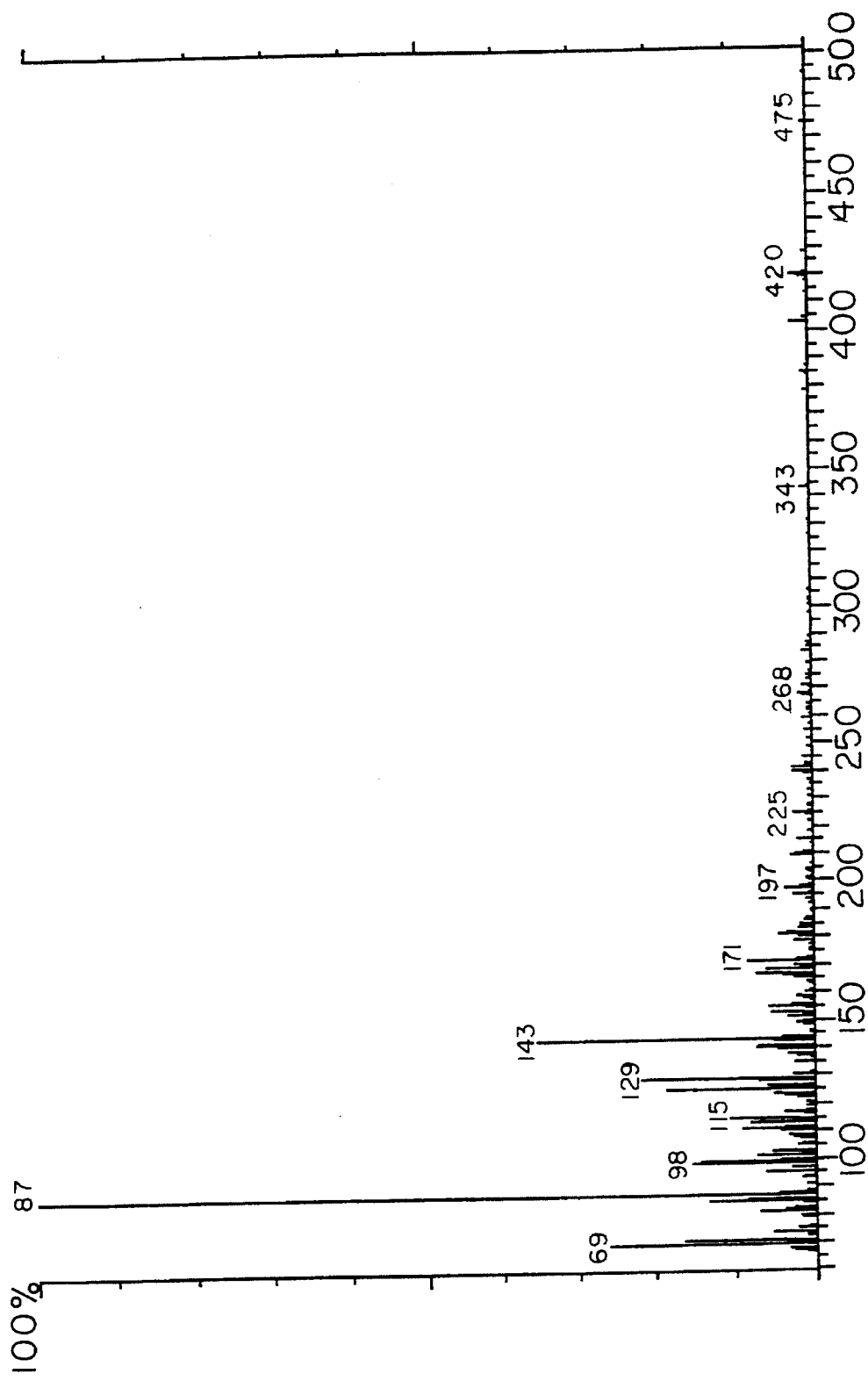

FIGS. 7a–c show the electron impact mass spectra of the fully acetylated 1-deoxy-1-(N,N'-diacetylhydrazino) alditols representative of particular classes of derivatives; in FIG. 7a for hexoses, that of the D-glucose derivative (with the spectrum obtained using lower filament power shown in the inset); in FIG. 7b, for pentoses, that of the D-ribose derivative; in FIG. 7c, for 2-acetamido-2-deoxyhexoses, that of 2-acetamido-2-deoxy-D-glucose; in FIG. 7d, for 6-deoxy-hexoses, that of L-rhamnose; and in FIG. 7e, for 3-O-methyl-hexoses, that of 3-O-methyl-D-glucose.

From the foregoing, it will be evident that, although specific embodiments of the invention have been described herein for purposes of illustration, various modifications may be made without deviating from the spirit and scope of the invention.

I claim:

1. A N,N'-diacetylhydrazino monosaccharide derivative having the following structure:

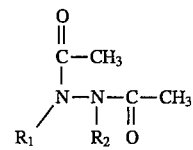

wherein $R_1$ is a 1-deoxy aldose or deoxy ketose moiety, and $R_2$ is hydrogen or an alkyl group containing 1–8 carbon atoms.

2. A monosaccharide derivative according to claim 1 wherein $R_2$ is an alkyl group containing 1–8 carbon atoms.

3. A monosaccharide derivative according to claim 1 wherein said derivative is fully acetylated.

4. A monosaccharide derivative according to claim 1 wherein $R_1$ has an O-methyl linkage.

5. An N,N'-diacetylhydrazino monosaccharide derivative wherein said monosaccharide derivative is produced according to the steps of:

(a) generating a hydrazone by reacting a monosaccharide with a hydrazine having the following structure:

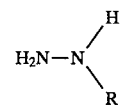

wherein R is hydrogen or an alkyl group containing 1–8 carbon atoms and wherein said monosaccharide is an aldose or a ketose;

(b) reducing the hydrazone to a hydrazino derivative; and (c) acetylating the hydrazino derivative under conditions such that acetylation occurs on the nitrogen atoms.

6. A monosaccharide derivative according to claim 5 wherein said monosaccharide is present at the reducing end of an oligosaccharide, and wherein the generation of said hydrazino derivative is achieved by the additional step of cleaving said monosaccharide derivative from the oligosaccharide.

7. A monosaccharide derivative according to claim 5 wherein R is an alkyl group containing 1–8 carbon atoms.

8. A monosaccharide derivative according to claim 5 wherein said derivative is fully acetylated.

9. A method for generating a N,N'-diacetylhydrazino monosaccharide derivative having the following structure:

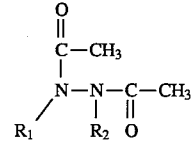

wherein $R_i$ is a 1-deoxy-aldose moiety or a deoxy ketose moiety, and $R_2$ is hydrogen or an alkyl group containing 1–8 carbon atoms, comprising the steps of:

(a) generating a hydrazone by reacting a monosaccharide with a hydrazine having the following structure:

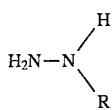

wherein R is hydrogen or an alkyl group containing 1–8 carbon atoms and wherein said monosaccharide is an aldose or a ketose;

(b) reducing the hydrazone to a hydrazino derivative; and (c) acetylating the hydrazino derivative under conditions such that acetylation occurs on the nitrogen atoms.

10. The method of claim 9, further comprising the step of acetylating the hydrazino derivative under conditions such that the hydrazino derivative is fully acetylated.

11. The method of either of claims 9 or 10 wherein R is an alkyl group containing 1 to 8 carbon atoms.

12. The method of either of claims 9 or 10 wherein said method is automated.

13. The method of either of claims 9 or 10, wherein the monosaccharide is present at the reducing end of an oligosaccharide, and wherein said method further comprises cleaving the glycosidic bond between the hydrazino derivative and the adjacent monosaccharide in the oligosaccharide.

14. The method of claim 13 wherein said method is automated.

15. A method for identifying an aldose or ketose monosaccharide comprising the steps of:

(a) generating a N,N'-diacetylhydrazino monosaccharide derivative according to the method of either of claims 9 or 10;

(b) separating said monosaccharide derivative by chromatography; and (c) analyzing the separated monosaccharide derivative to determine the identity.

16. The method of claim 15 wherein said step of analyzing comprises analysis by mass spectrometry.

17. The method of claim 16 wherein said mass spectrometry is on-line.

18. The method of claim 15 wherein said step of analyzing comprises analysis by ultraviolet spectrophotometry.

19. The method of claim 15 wherein said method is automated.

20. A method for identifying an aldose or ketose monosaccharide present at the reducing end of an oligosaccharide comprising the steps of:

(a) generating an acetylated hydrazino monosaccharide derivative according to the method of claim 13;

(b) separating said monosaccharide derivative by chromatography; and (c) analyzing the separated monosaccharide derivative to determine the identity.

21. The method of claim 20 wherein said step of analyzing comprises analysis by mass spectrometry.

22. The method of claim 21 wherein said mass spectrometry is on-line.

23. The method of claim 20 wherein said step of analyzing comprises analysis by ultraviolet spectrophotometry.

24. The method of claim 20 wherein said method is automated.

\* \* \* \* \*

UNITED STATES PATENT AND TRADEMARK OFFICE
CERTIFICATE OF CORRECTION

PATENT NO.   :  5,585,473
DATED        :  December 17, 1996
INVENTOR(S)  :  Brad K. Bendiak It is certified that error appears in the above identified patent and that said Letters Patent is hereby corrected as shown below:

In column 44, claim 9, line 63, please delete "$R_i$" and insert therefor --$R_1$--.

Signed and Sealed this

Thirteenth Day of May, 1997

Attest:

BRUCE LEHMAN

Attesting Officer

Commissioner of Patents and Trademarks